(12) United States Patent
Pahan

(10) Patent No.: US 9,006,205 B2
(45) Date of Patent: Apr. 14, 2015

(54) ANTISENSE OLIGONUCLEOTIDES AGAINST NEUTRAL SPHINGOMYELINASE AND NEUTRAL SPHINGOMYELINASE INHIBITOR GW4869 FOR DEGENERATIVE NEUROLOGICAL DISORDERS

(75) Inventor: Kalipada Pahan, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 14/118,725

(22) PCT Filed: May 21, 2012

(86) PCT No.: PCT/US2012/038757
§ 371 (c)(1),
(2), (4) Date: May 28, 2014

(87) PCT Pub. No.: WO2012/162211
PCT Pub. Date: Nov. 29, 2012

(65) Prior Publication Data
US 2014/0275210 A1    Sep. 18, 2014

Related U.S. Application Data

(60) Provisional application No. 61/488,256, filed on May 20, 2011.

(51) Int. Cl.
| | |
|---|---|
| *A61K 48/00* | (2006.01) |
| *C07H 21/02* | (2006.01) |
| *C07H 21/04* | (2006.01) |
| *A61K 38/00* | (2006.01) |
| *A61P 25/28* | (2006.01) |
| *A61K 31/4178* | (2006.01) |

(Continued)

(52) U.S. Cl.
CPC ........ *C12N 15/1137* (2013.01); *A61K 31/4178* (2013.01); *A61K 31/7088* (2013.01); *A61K 2300/00* (2013.01); *C12N 2310/11* (2013.01); *C12Y 301/04012* (2013.01)

(58) Field of Classification Search
USPC ........................................ 514/2, 44; 536/24.5
See application file for complete search history.

(56) References Cited

FOREIGN PATENT DOCUMENTS

| | | |
|---|---|---|
| DE | 10352449 A1 | 6/2005 |
| WO | WO 03/102244 A1 | 12/2003 |

(Continued)

OTHER PUBLICATIONS

Chen et al., "Amyloid beta peptide increases DP5 expression via activation of neutral sphingomyelinase and JNK in oligodendrocytes," Jounal of Neurochemistry, 2006, 97, pp. 631-640, XP008095311.

(Continued)

*Primary Examiner* — Terra Cotta Gibbs
(74) *Attorney, Agent, or Firm* — Brinks Gilson & Lione

(57) ABSTRACT

Alzheimer's disease (AD) is the most common human neurodegenerative disease of the CNS resulting in progressive neuronal death and memory loss. Despite intense investigations, no effective therapy is available to stop its onset or halt its progression. It was discovered that antisense oligonucleotide against neutral sphingomyelinase and GW4869, a chemical inhibitor of neutral sphingomyelinase, inhibit activation of glial cells and protect neurons in AD cell culture and animal models. These results suggest the following new treatment options for AD patients: Antisense oligonucleotide against neutral sphingomyelinase and GW4869.

4 Claims, 11 Drawing Sheets

(51) Int. Cl.
*A61K 31/7088* (2006.01)
*C12N 15/113* (2010.01)

(56) References Cited

FOREIGN PATENT DOCUMENTS

WO  WO 2005/012514 A1  2/2005
WO  WO 2012/162211 A2  11/2012

OTHER PUBLICATIONS

Grimm et al., "Amyloid beta as a regulator of lipid homostasis," Trends in Molecular Medicine, vol. 13, No. 8, ScienceDirect, 2007 Elsevier Ltd., pp. 337-334.

Jana et al., "Human Immunodeficiency Virus Type 1 gp120 Induces Apoptosis in Human Primary Neurons through Redox-Regulated Activation of Neutral Sphingomyelinase," Neurobiology of Disease, The Journal of Neuroscience, Oct. 27, 2009. 24, (43), pp. 9531-9540.

Jana et al., "Fibrillar Amyloid-β-Activated Human Astroglia Kill Primary Human Neurons via Neutral Sphingomyelinase; Implications for Alzheimer's Disease," The Journal of Neuroscience, Sep. 22, 2010, 30(38), pp. 12676-1289, Department of Neurological Science, Rush University Medical Center.

Jana et al., "Fibriller Amyloid-β-Peptides Kill Human Primary Neurons via NADPH Oxidase-mediated Activation of Neutral Sphingomyelinase," The Journal of Biological Chemistry, 2004 by The American Society of Biochemistry and Molecular Biology, Inc., vol. 29., No. 41, Issue of Dec. 8, pp. 51451-51459.

Jana et al., "Ceramide and neurodegeneration: Susceptibility of neurons and oligodendrocytes to cell damage and death," Journal of the Neurological Sciences, 278, (2009), pp. 5-15.

Lee et al., "Amyloid-β peptide induces oligodendrocyte death by activating the neurtral sphingomyelinase-ceramide pathway," The Jouranl of Cell Biology, vol. 164, No. 1, Jan. 5, 2004, pp. 123-131.

Malaplate-Armand et al., "Soluble oligomers of amyloid-β peptide induce neuronal apoptosis by activating a $cPLA_2$-dependent sphingomyelinase-ceramide pathway," Neurobiology of Disease 23, (2006) pp. 178-189.

Wu et al., "Mammaliam Neutral Sphingomyelinases: Regulation and Roles in Cell Signaling Responses," Neuromol Med., (2010) 12:320-330, Humana Press.

Yang et al., "Neutral sphingomyelinase activation in endothelial and glial cell death induced by amyloid beta-peptide," Elsevier, Neurobiology of Disease, 17 (2004), pp. 99-107.

PCT International Search Report for International No. PCT/US2012/038757, date of actual completion Oct. 9, 2012. 8 pages.

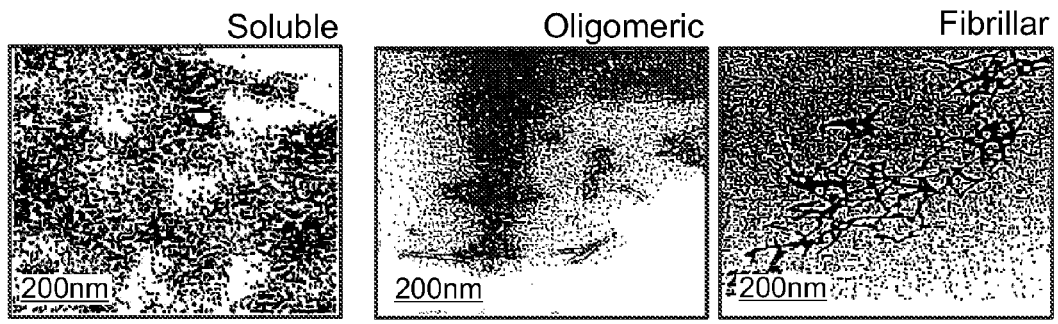
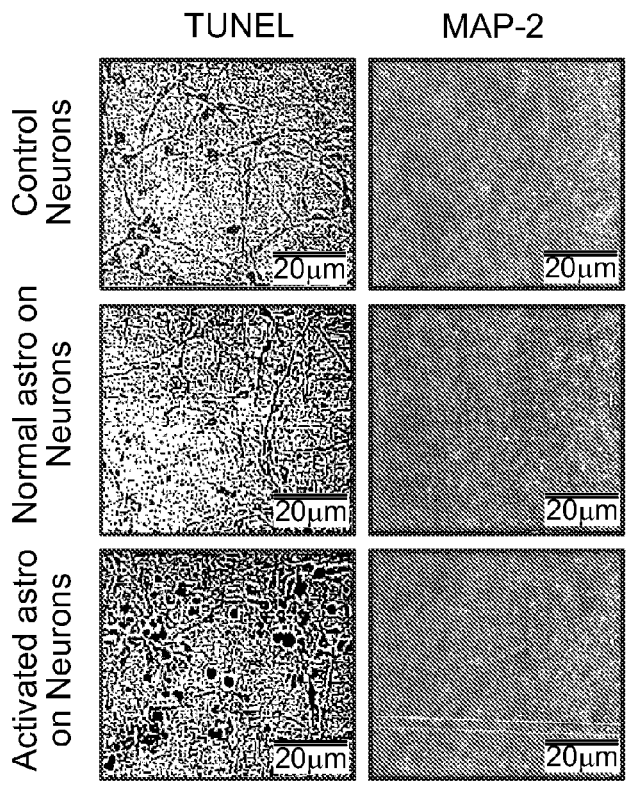
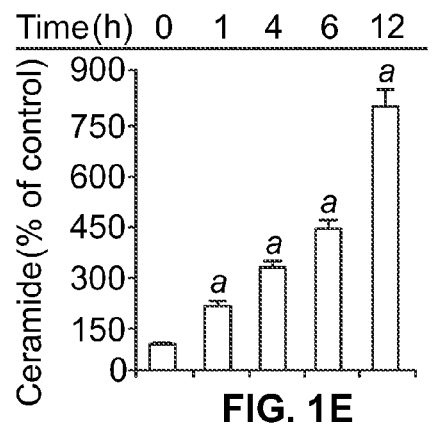
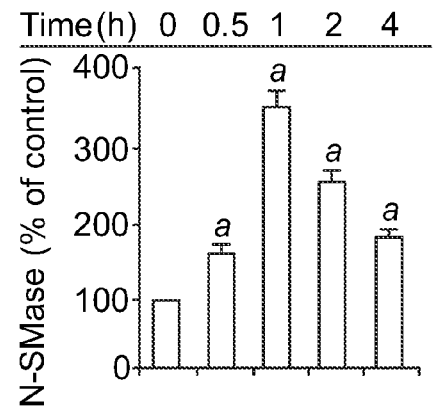
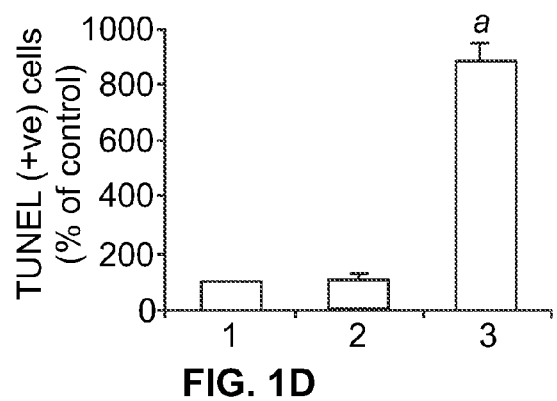
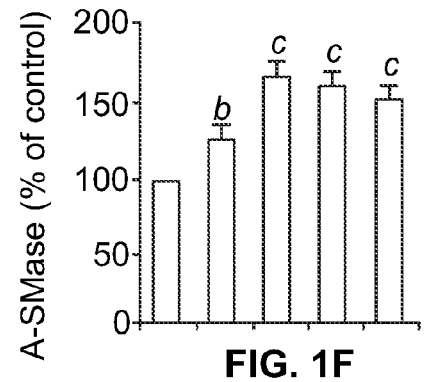

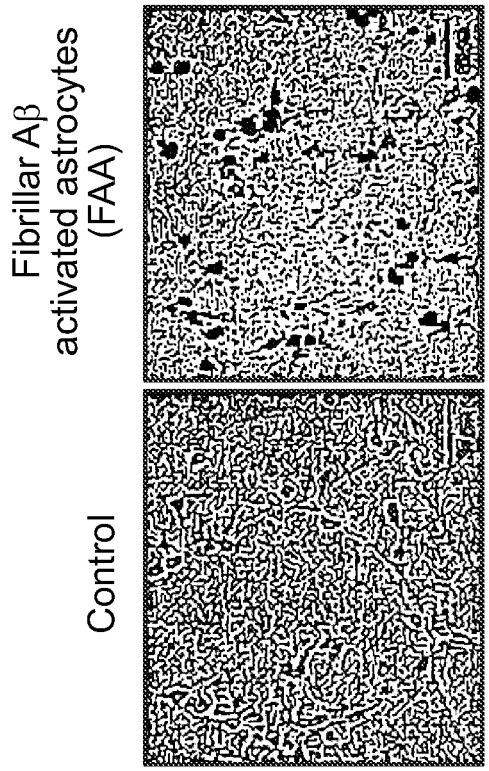
FIG. 2A
FIG. 2B
FIG. 2C

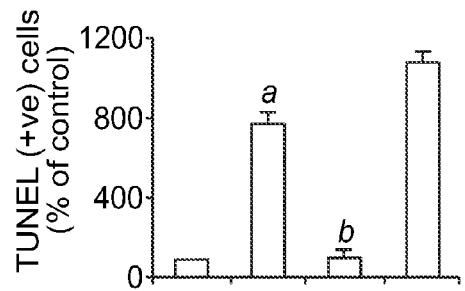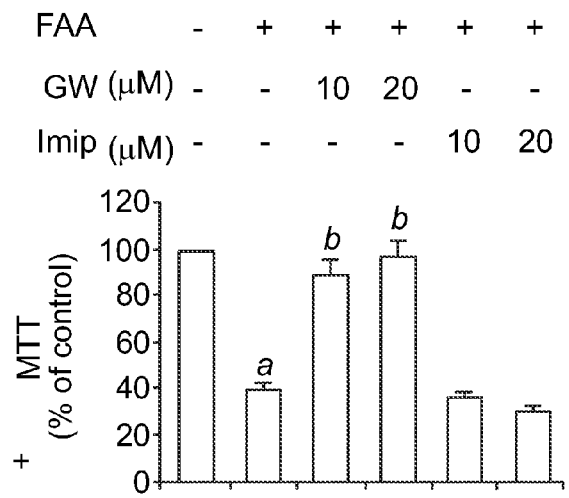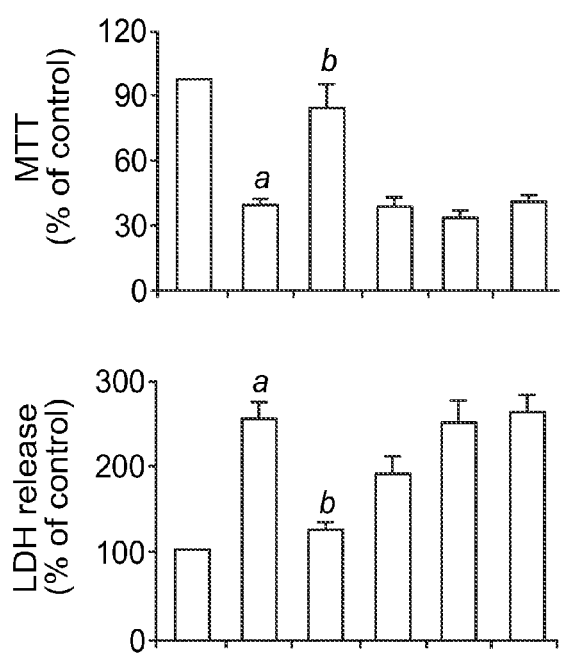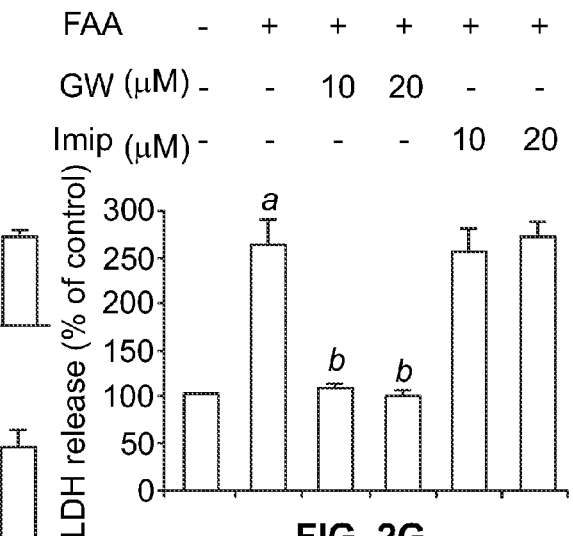
FIG. 2D
FIG. 2F
FIG. 2E
FIG. 2G

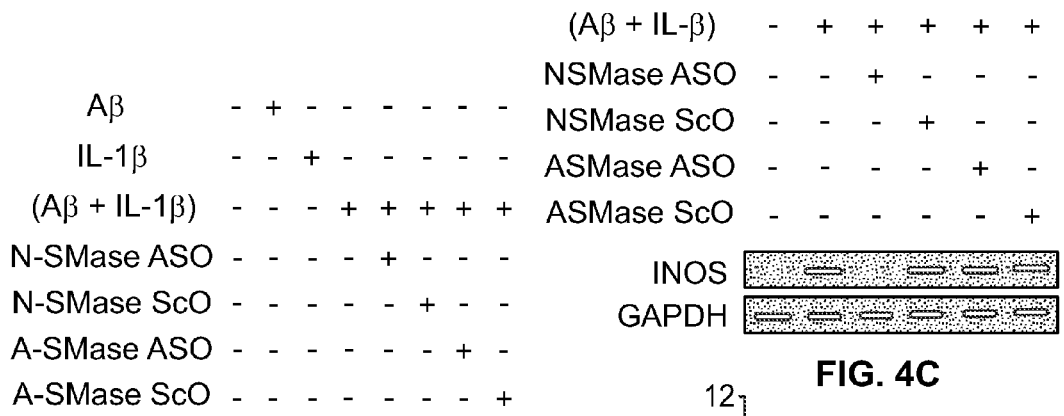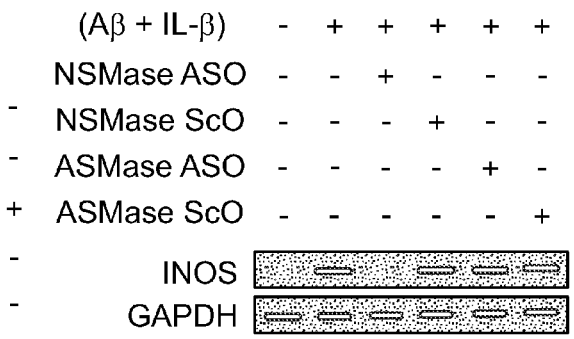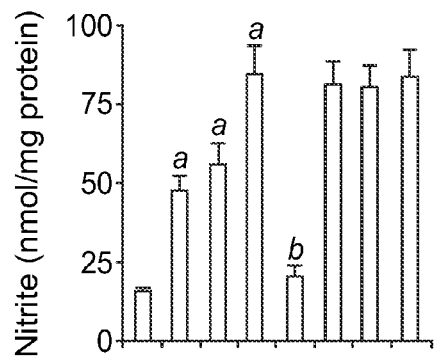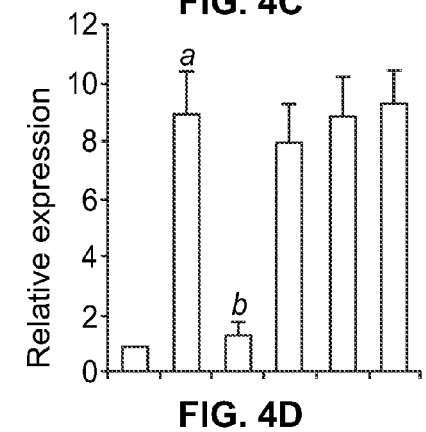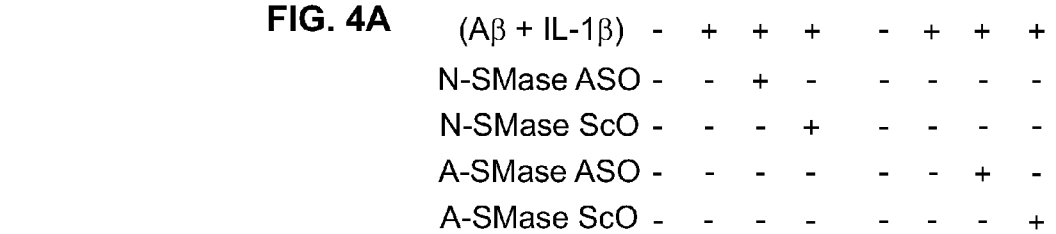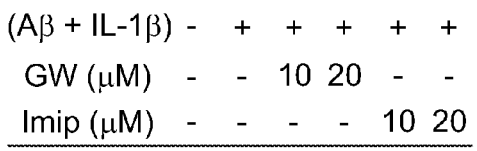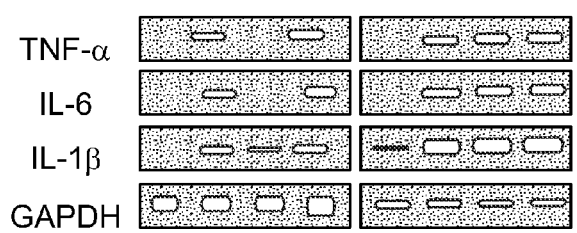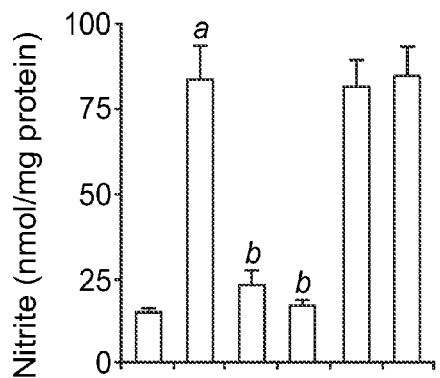
FIG. 4A
FIG. 4B
FIG. 4C
FIG. 4D
FIG. 4E

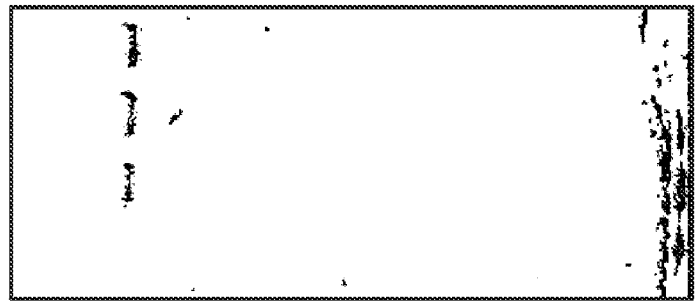
FIG. 6C
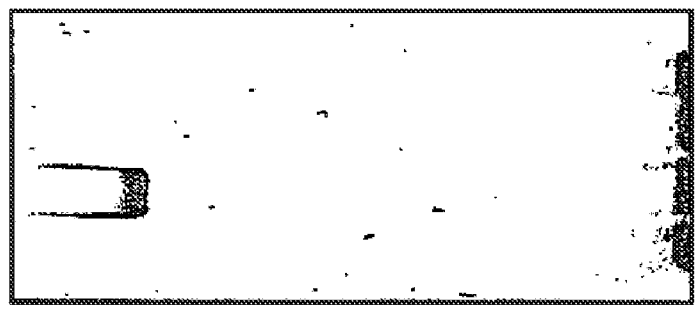
FIG. 6B
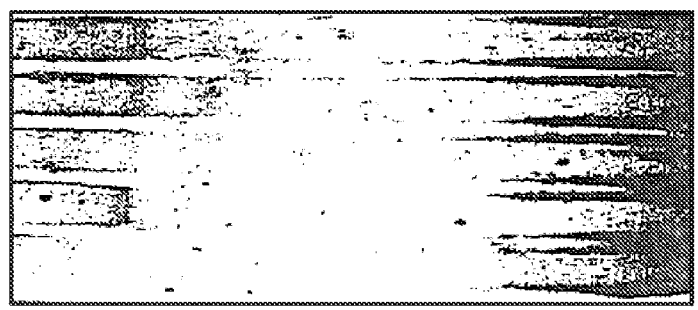
FIG. 6A
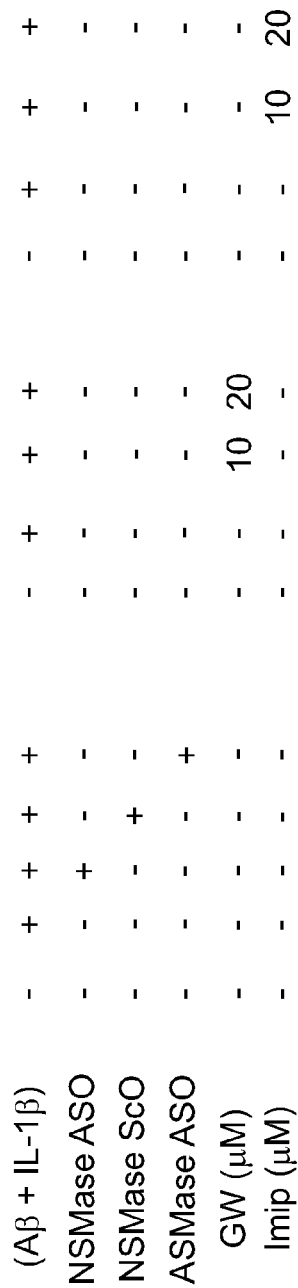

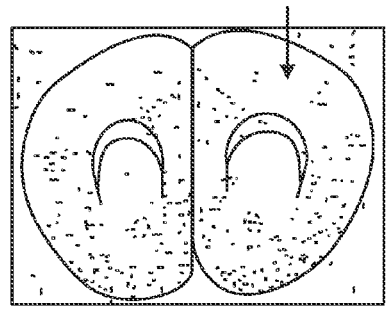
FIG. 7A
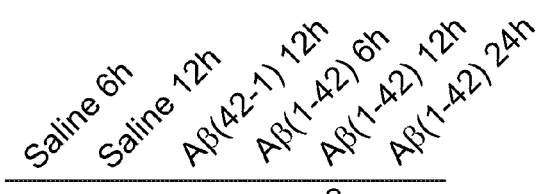
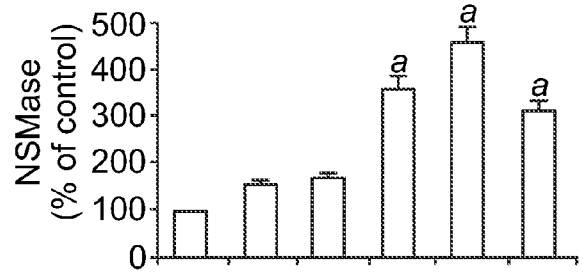
FIG. 7B
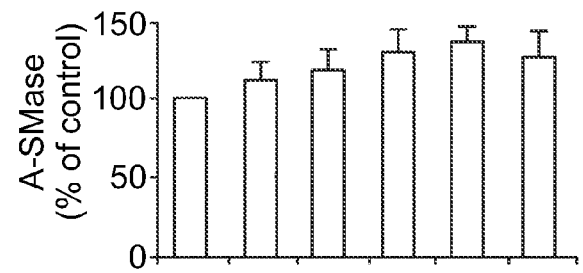
FIG. 7C
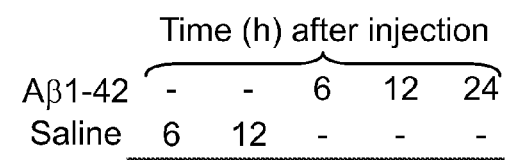
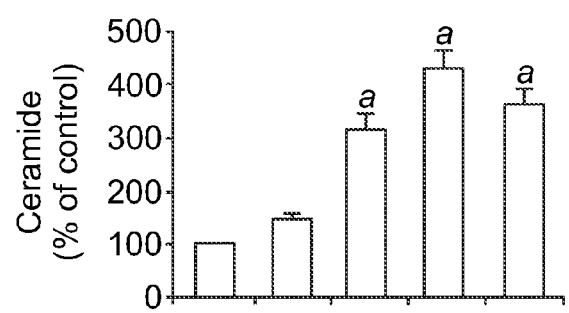
FIG. 7D

```
                        SEQUENCE LISTING

<160> NUMBER OF SEQ ID NOS: 17

<210> SEQ ID NO 1
<211> LENGTH: 25
<212> TYPE: DNA
<213> ORGANISM: artificial
<220> FEATURE:
<223> OTHER INFORMATION: TNF forward primer

<400> SEQUENCE: 1
ctgagtcggt cacccttctc cagct                                            25

<210> SEQ ID NO 2
<211> LENGTH: 25
<212> TYPE: DNA
<213> ORGANISM: Artificial Sequence
<220> FEATURE:
<223> OTHER INFORMATION: TNF reverse primer

<400> SEQUENCE: 2
cccgagtgac aagcctgtag cccat                                            25

<210> SEQ ID NO 3
<211> LENGTH: 20
<212> TYPE: DNA
<213> ORGANISM: Artificial Sequence
<220> FEATURE:
<223> OTHER INFORMATION: IL-1B forward primer

<400> SEQUENCE: 3
ggatatggag caacaagtgg                                                  20

<210> SEQ ID NO 4
<211> LENGTH: 19
<212> TYPE: DNA
<213> ORGANISM: Artificial Sequence
<220> FEATURE:
<223> OTHER INFORMATION: IL-1B reverse primer

<400> SEQUENCE: 4
atgtaccagt tggggaact                                                   19

<210> SEQ ID NO 5
<211> LENGTH: 24
<212> TYPE: DNA
<213> ORGANISM: Artificial Sequence
<220> FEATURE:
<223> OTHER INFORMATION: IL-6 forward primer

<400> SEQUENCE: 5
ttttggagtt tgaggtatac ctag                                             24
```

<210> SEQ ID NO 6
<211> LENGTH: 24
<212> TYPE: DNA
<213> ORGANISM: Artificial Sequence
<220> FEATURE:
<223> OTHER INFORMATION: IL-6 reverse primer

<400> SEQUENCE: 6
gctgcgcaga atgagatgag ttgt                                              24

<210> SEQ ID NO 7
<211> LENGTH: 25
<212> TYPE: DNA
<213> ORGANISM: Artificial Sequence
<220> FEATURE:
<223> OTHER INFORMATION: iNOS forward primer

<400> SEQUENCE: 7
ctgcagacac gtgcgttact ccacc                                             25

<210> SEQ ID NO 8
<211> LENGTH: 25
<212> TYPE: DNA
<213> ORGANISM: Artificial Sequence
<220> FEATURE:
<223> OTHER INFORMATION: iNOS reverse primer

<400> SEQUENCE: 8
gcagggcgta ccactttagc tccag                                             25

<210> SEQ ID NO 9
<211> LENGTH: 20
<212> TYPE: DNA
<213> ORGANISM: Artificial Sequence
<220> FEATURE:
<223> OTHER INFORMATION: GADPH forward primer

<400> SEQUENCE: 9
ggtgaaggtc ggagtcaacg                                                   20

<210> SEQ ID NO 10
<211> LENGTH: 20
<212> TYPE: DNA
<213> ORGANISM: Artificial Sequence
<220> FEATURE:
<223> OTHER INFORMATION: GADPH reverse primer

<400> SEQUENCE: 10
gtgaagacgc cagtggactc                                                   20

<210> SEQ ID NO 11
<211> LENGTH: 22
<212> TYPE: DNA
<213> ORGANISM: Artificial Sequence
<220> FEATURE:
<223> OTHER INFORMATION: NF-KF consensus binding sequence

<400> SEQUENCE: 11
agttgagggg actttcccag gc                                                22

<210> SEQ ID NO 12
<211> LENGTH: 21
<212> TYPE: DNA
<213> ORGANISM: Artificial Sequence
<220> FEATURE:
<223> OTHER INFORMATION: N-SMase ASO

```
<400> SEQUENCE: 12
cagcgagccc gtccaccagc c                                              21

<210> SEQ ID NO 13
<211> LENGTH: 21
<212> TYPE: DNA
<213> ORGANISM: Artificial Sequence
<220> FEATURE:
<223> OTHER INFORMATION: N-SMase ScO

<400> SEQUENCE: 13
cacgcgtccg acgccgcacg a                                              21

<210> SEQ ID NO 14
<211> LENGTH: 20
<212> TYPE: DNA
<213> ORGANISM: Artificial Sequence
<220> FEATURE:
<223> OTHER INFORMATION: A-SMase ASO

<400> SEQUENCE: 14
gacatctcgg agccggggca                                                20

<210> SEQ ID NO 15
<211> LENGTH: 20
<212> TYPE: DNA
<213> ORGANISM: Artificial Sequence
<220> FEATURE:
<223> OTHER INFORMATION: A-SMase ScO

<400> SEQUENCE: 15
ggaaacccgg ttaggcccgg                                                20

<210> SEQ ID NO 16
<211> LENGTH: 21
<212> TYPE: DNA
<213> ORGANISM: Artificial Sequence
<220> FEATURE:
<223> OTHER INFORMATION: mN-SMase ASO

<400> SEQUENCE: 16
cagcgagccg gtccaccagc c                                              21

<210> SEQ ID NO 17
<211> LENGTH: 21
<212> TYPE: DNA
<213> ORGANISM: Artificial Sequence
<220> FEATURE:
<223> OTHER INFORMATION: mN-SMase ScO

<400> SEQUENCE: 17
cacgcgtccg acgccgcacg a                                              21
```

ANTISENSE OLIGONUCLEOTIDES AGAINST NEUTRAL SPHINGOMYELINASE AND NEUTRAL SPHINGOMYELINASE INHIBITOR GW4869 FOR DEGENERATIVE NEUROLOGICAL DISORDERS

This application claims the benefit under 35 U.S.C. §371 of International Application No. PCT/US2012/038757, filed May 21, 2012, which claims the benefit of U.S. Provisional Application No. 61/488,256, filed May 20, 2011, which are incorporated by reference herein in their entirety.

BACKGROUND

1. Technical Field

This disclosure related to the treatment of Alzheimer's disease (AD), the most common human neurodegenerative disease of the CNS resulting in progressive neuronal death and memory loss. More specifically, an antisense oligonucleotide against neutral sphingomyelinase and GW4869, a chemical inhibitor of neutral sphingomyelinase, are shown to inhibit activation of glial cells and protect neurons in AD cell culture and animal models. As a result, new treatment options for AD patients are disclosed.

2. Description of the Related Art

Alzheimer's disease (AD) is a neurodegenerative disorder resulting in progressive neuronal death and memory loss. Neuropathologically, the disease is characterized by neurofibrillary tangles and neuritic plaques. Neurofibrillary tangles are composed of the hyperphosphorylated tau protein. On the other hand, neuritic plaques are mainly composed of aggregates of amyloid-β (Aβ) protein, a 40-43 amino acid proteolytic fragment derived from the amyloid precursor protein (APP) that is over-expressed in AD (Martin, 1999). Histopathologically, this disease is characterized by infiltration of inflammatory cells into the CNS, gliosis, and neuronal apoptosis.

Although deposition of Aβ peptides is one of the primary causes of neuronal loss in AD, mechanisms by which Aβ causes neuronal loss are largely unknown. Several lines of evidence suggest that neurons are killed through neurotoxic molecules elaborated from glial activation. Consequently, activated astrocytes and microglia are characteristically found in abundance near amyloid plaques in AD and in mouse models of AD, and amyloid peptides have been reported as glial activators in the presence of an immunological co-factor. Activated glia are also found to increase substantially in the hippocampus and neocortex of the aging brain. Consistently, microinjection of pre-aggregated Aβ1-42 peptides into the nucleus basalis of the rat produces a congophylic deposit followed by microglial and astrocyte activation and a strong inflammatory reaction surrounding the dystrophic neuritis.

Therefore, controlling glial activation and hence inflammation are of great therapeutic interest in mitigating neuronal cell death in different neurological disorders including AD. Because ceramide, the lipid second messenger molecule, produced from the degradation of sphingomyelin by sphingomyelinases (neutral and acidic) induces apoptosis and cell death in various cell types, including glial and neuronal cells. It was decided to investigate the N-SMase-ceramide pathway in Aβ-activated glia-mediated neuronal death. Here, the evidence that (A+IL-i)-activated astrocytes induce the activation of sphingomyelinases and the production of ceramide in human primary neurons is presented. The activation of neutral, but not acidic, sphingomyelinase plays a key role in neuronal apoptosis in response to neurotoxins released from activated astrocytes is shown. Further, blocking of astroglial activation by N-SMase inhibition prevented the release of neurotoxic substances. Subsequently, inhibition of astroglial N-SMase suppressed NF-κB activation in activated astroglia. The in vitro data were further substantiated by in vivo findings where it has been found that antisense oligonucleotides against N-SMase prevented astrogliosis and microgliosis and protected neurons in the cortex of Aβ-injected C57/BL6 mice.

SUMMARY OF THE DISCLOSURE

This disclosure illustrates that Aβ plus interleukin-1β (Aβ+IL-1β)-activated astrocytes induce the activation of sphingomyelinases and the production of ceramide in human primary neurons. It is shown that the activation of neutral sphingomyelinase, but not acidic sphingomyelinase (A-SMase), plays a key role in neuronal apoptosis in response to neurotoxins released from activated astrocytes. Furthermore, blocking of astroglial activation by N-SMase inhibition prevented the release of neurotoxic substances. Subsequently, inhibition of astroglial N-SMase suppressed nuclear factor-κβ (NF-κβ) activation in activated astroglia. The in vitro data were further substantiated by in vivo findings where it has been found that antisense oligonucleotides (ASOs) against N-SMase prevented astrogliosis and microgliosis and protected neurons in the cortex of AP-injected C57BL/6 mice.

Glial activation plays an important role in the pathogenesis of various neurodegenerative disorders including Alzheimer's disease (AD). However, molecular mechanisms by which activated glia could kill neurons are poorly understood. This disclosure underlines the importance of neutral sphingomyelinase (N-SMase) in mediating the damaging effect of fibrillar amyloid-β 1-42 (Aβ1-42) peptide-activated astroglia on neurons. In trans-well experiments, soluble products released from activated primary human astroglia induced the activation of neutral sphingomyelinase (N-SMase), production of ceramide and cell death in primary human neurons. Protection of neurons from cytotoxic effects of activated astroglia by antisense knockdown of N-SMase, but not acidic sphingomyelinase (A-SMase), suggests that soluble products released from activated astroglia kill neurons via N-SMase, but not A-SMase. Next, an examined the role of N-SMase in the activation of human astroglia was carried out. Interestingly, knockdown of N-SMase, but not A-SMase, by either antisense oligonucleotides or chemical inhibitor prevented the induction of proinflammatory molecules (TNF-a, iNOS, IL-Iβ, and IL-6) and the activation of NF-κB in Aβ 1-42-activated astroglia. Subsequently, fibrillar Aβ peptides also induced the activation of N-SMase and ceramide in vivo in mouse cortex. Most importantly, antisense knockdown of N-SMase, but not A-SMase, decreased the activation of astroglia and protected neurons from fibrillar Aβ toxicity in vivo in the cortex. Taken together, it is apparent that both the activation of astroglia by Aβ and that the cytotoxicity of activated astroglia on neurons depend on N-SMase.

Therefore, in one aspect, a composition is disclosed for the treatment of a neurodegenerative disorder. The disclosed composition includes an antisense oligonucleotide against netural sphingomyelinase.

In another aspect, a composition is disclosed for the treatment of a neurodegenerative disorder. This disclosed composition includes GW4869.

In yet another aspect, a composition for the treatment of a neurodegenerative disorder is disclosed. The disclosed composition includes an antisense oligonucleotide against netural sphingomyelinase and GW4869.

In any one or more of the embodiments described above, the neurodegenerative disorder may be selected from the group consisting of Alzheimer's disease, Parkinson's disease, multiple sclerosis, Huntington's disease and combinations thereof.

A method of treating neurodegenerative disorders in mammals as also disclosed that includes any one of administering an antisense oligonucleotide against netural sphingomyelinase, administering GW4869 and/or administering an antisense oligonucleotide against netural sphingomyelinase and GW4869.

Other advantages and features will be apparent from the following detailed description when read in conjunction with the attached drawings.

BRIEF DESCRIPTION OF THE DRAWINGS

FIGS. 1A-1F illustrate photographically and graphically that activated primary human astrocytes induce apoptosis and the activation of the N-SMase-ceramide pathway in primary human neurons in neuron-astrocyte transwell cultures.

FIGS. 2A-2G illustrates graphically and photographically that antisense or chemical knockdown of N-SMase, but not A-SMase, protects neurons from Aβ-activated primary human astrocytes in astrocyte-neuron transwell cultures.

FIGS. 4A-4E illustrate graphically that antisense and chemical knockdown of N-SMase, but not A-SMase, blocks the expression of iNOS and proinflammatory cytokines in Aβ+IL-i-activated primary human astrocytes.

FIGS. 6A-6C graphically illustrate that the inhibition of N-SMase, but not A-SMase, suppresses the activation of NF-κβ in activated primary human astrocytes.

FIGS. 7A-7D graphically illustrate that fibrillar Aβi$_{42}$ peptides induce the activation of N-SMase and the production of ceramide in vivo in the cortex of C57BL/6 mice.

Figure 3A:
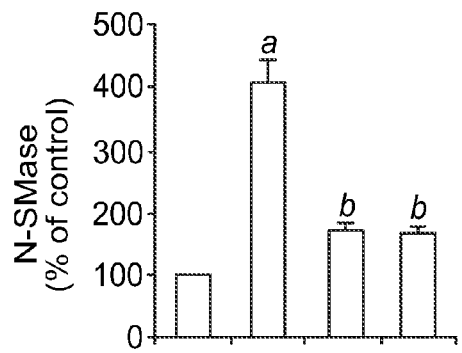
FIGS. 3A-3E illustrate the role of nitric oxide in activated astrocyte-induced cell death in neurons.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Materials and Methods

Reagents—

Neurobasal medium and B27 supplement were purchased from Invitrogen. Fetal bovine serum and DMEM/F-12 were obtained from Mediatech (Ormond Beach, Fla.). Human Aβ peptides (1-42) and (42-1) were obtained from Bachem Bioscience. Glial fibrillary acidic protein (GFAP) was purchased from Santa Cruz Biotechnology. Phosphorothioate-labeled antisense and scrambled oligodeoxynucleotides were synthesized in the DNA-synthesizing facility of Invitrogen.

Isolation of Primary Human Neurons—

Human primary neurons were prepared as described by us earlier. All of the experimental protocols were reviewed and approved by the Institutional Review Board of the Rush University Medical Center. Briefly, 11-17-week-old fetal brains obtained from the Human Embryology Laboratory (University of Washington, Seattle, Wash.) were dissociated by trituration and trypsinization (0.25% trypsin in PBS at 37° C. for 15 min). The trypsin was inactivated with 10% heat-inactivated fetal bovine serum (Mediatech). The dissociated cells were filtered through 380- and 140-μm meshes (Sigma) and pelleted by centrifugation. The cell pellet was washed once with PBS and once with Neurobasal medium containing 2% B27 and 1% antibiotic-antimycotic mixture (Sigma). In the first step, neurons were enriched by allowing the cells ($3 \times 10^6$/ml) to adhere to poly-D-lysine-coated plates or coverslips for 5 min. Nonadherent cells were removed, and adherent cells (mostly neurons) were further treated with 10 μM Ara-C to prevent the proliferation of dividing cells. After 10 days of Ara-C treatment, the cells were used for this study. More than 98% of this preparation was positive for microtubule-associated protein-2 (MAP-2), a marker for neurons.

Preparation of Primary Human Astrocytes—Primary human astrocytes were prepared as described by us earlier. Briefly, human CNS tissue (Human Embryology Laboratory, University of Washington, Seattle) from each specimen was processed separately and independently, as were subsequent cell cultures. There was no pooling of CNS tissue from distinct specimens. All of the experimental protocols were reviewed and approved by the Institutional Review Board of the Rush University Medical Center. By immunofluorescence assay, these cultures homogeneously expressed glial fibrillary acidic protein (GFAP).

Astrocyte-Neuron Trans-well Study—

Primary human astrocytes were grown to confluency on inserts. After 24 h of stimulation by the combination of Aβ (1 μM) and IL-Iβ (10 ng/ml), inserts were washed thrice with HBSS and then placed onto the wells containing primary human neurons. Therefore, in this trans-well model, although neurons and astrocytes face each other, they are separable and the effect of soluble factors released from activated astrocytes on neurons can be studied allowing analysis of neuronal and glial populations separately.

Preparation of Fibrillar Aβ—

Fibrillar Aβ1-42 and control reverse peptide Aβ42-1 (Bachem Bioscience) were prepared by incubating freshly solubilized peptides at 50 μM in sterile distilled water at 37° C. for 5 days. On the other hand, oligomeric Aβ1-42 was prepared after incubation at 37° C. for 2 days. Please see FIG. 1A for morphology of oligomeric and fibrillar forms of Aβ1-42.

Treatment of Primary Neurons—

During treatment with fibrillar Aβ peptides, cells were incubated in Neurobasal medium containing 2% B27 supplement without antioxidant (B27-AO) (Invitrogen).

Assay of Neutral and Acidic Sphingomyelinases (N-SMase and A-SMase)—

Activities of SMase(s) were assayed as described by. Briefly, after treatment, the cells were washed with PBS, harvested in PBS, divided into two halves, and centrifuged. The fraction for N-SMase was resuspended in buffer A (100 mM Tris-HCl, pH 7.4, 0.1% Triton X-100, 1 mM EDTA, and protease inhibitors), and the cell suspension was sonicated and centrifuged at 500×g at 4° C. for 5 min. The supernatant was used as the enzyme source for N-SMase. The reaction mixture contained enzyme preparation in buffer A containing 5 nmol of [$^{14}$C] sphingomyelin, 5 nmol of phosphatidylserine, 5 mM dithiothreitol, and 5 mM MgC¾ in a final volume of 100 μl. Similarly, the fraction for A-SMase was resuspended in buffer B (100 mM sodium acetate, pH 5.0, 0.1% Triton X-100, and protease inhibitors). The cell suspension was sonicated and centrifuged. The supernatant was used as the source of A-SMase. The activity of A-SMase was measured in a 100-μl reaction mixture consisting of the enzyme preparation in buffer B and 5 nmol of [$^{14}$C] sphingomyelin. The enzyme reaction was initiated by the addition of 50 μl of substrate and stopped by the addition of 1.5 ml of chloroform:methanol (2:1, v/v) and 0.2 ml of water. After vortexing and phase separation, the aqueous phase was removed for counting.

Quantification of Ceramide Levels by Diacylglycerol Kinase Assay—

After treatment, lipids were extracted from cells as described previously. Ceramide content was quantified using diacylglycerol (DAG) kinase and [$\gamma$-$^{32}$P] ATP as described earlier. Briefly, dried lipids were solubilized in 20 μl of an octyl β-D-glucoside/cardiolipin solution (7.5% octyl β-D-glucoside, 5 mM cardiolipin in 1 mM diethylenetriaminepentaacetic acid) by sonication in a sonicatorbath. The reaction was then carried out in a final volume of 100 μl containing the 20-μl sample solution, 50 mM imidazole HQ, pH 6.6, 50 mM NaCl, 12.5 mM MgCl$_2$, 1 mM EGTA, 2 mM dithiothreitol, 6.6 μg of DAG kinase, and 1 mM [$\gamma$-$^{32}$P] ATP (specific activity of 1-5×10$^5$ cpm/nmol) for 30 min at room temperature. The labeled ceramide-1-phosphate was resolved with a solvent system consisting of methyl acetate:n-propyl alcohol:chloroform:methanol:0.25% KQ in water:acetic acid (100:100:100:40:36:2). A standard sample of ceramide was phosphorylated under identical conditions and developed in parallel. Both standard and experimental samples had an identical R$_F$ value (0.46). Quantification of ceramide-1-phosphate was carried out by autoradiography and densitometry scanning using a Fluor Chem 8800 imaging system (Alpha Innotech Corporation). Values are expressed either as arbitrary units (absorbance) or as percent of control, considering control as 100%. Statistical comparisons were made using one-way analysis of variance followed by Student's t test.

Assay for NO Synthesis—

Synthesis of NO was determined by assay of culture supernatants for nitrite, a stable reaction product of NO with molecular oxygen, using Griess reagent as described.

Immunostaining—

Coverslips containing 200-300 cells/mm$^2$ were fixed with 4% paraformaldehyde for 20 min followed by treatment with cold ethanol (−20° C.) for 5 min and 2 rinses in PBS. The samples were blocked with 3% bovine serum albumin in PBS containing Tween 20 (PBST) for 30 min and incubated in PBST containing 1% bovine serum albumin and goat anti-MAP-2 (1:50), as described previously. After three washes in PBST (15 min each), the slides were further incubated with Cy5 (Jackson ImmunoResearch Laboratories, Inc.). For negative controls, a set of culture slides were incubated under similar conditions without the primary antibodies. The samples were mounted and observed under a Bio-Rad MRC1024ES confocal laser scanning microscope.

GFAP and NeuN Immunostaining—

Two days after microinjection, mice were perfused with 4% paraformaldehyde and their brains were processed for immunohistochemical studies. For double labeling of GFAP with iNOS, sections (6 μm) were incubated with polyclonal anti-GFAP (GFAP: 1000 dilution; Calbiochem) and anti-iNOS (iNOS: 1000 dilution; Calbiochem) for 24 h at 4° C. After three washes in PBST (15 min each), slides were further incubated with Cy5 and Cy2 (Jackson ImmunoResearch Laboratories, Inc.) secondary antibodies for 2 h at room temperature. For negative controls, a set of tissue sections was incubated under similar conditions without the primary antibodies. The samples were mounted and observed under a Bio-Rad MRC1024ES confocal laser scanning microscope.

Fragment End Labeling of DNA—

Fragmented DNA was detected in situ by the terminal deoxynucleotidyltransferase-mediated binding of 3'-OH ends of DNA fragments generated in response to fibrillar Aβ1-42, using a commercially available kit (TdT FragEL™) from Calbiochem. Briefly, cover slips were treated with 20 μg/ml proteinase K for 15 min at room temperature and washed prior to terminal deoxynucleotidyltransferase staining.

Cell Viability Measurement

MTT Assay—

Mitochondrial activity was measured with the 3-(4,5-dimethylthiazol-2-yl)-2,5-diphenyltetrazolium bromide (MTT) assay (Sigma). The cells were grown on 24-well culture plates with 500 μl of medium and treated with various reagents according to the experimental design. At the end of the treatment period, 300 μl of culture medium were removed from each well, and 20 μl of MTT solution (5 mg/ml) were added and incubated for 1 h.

Lactate Dehydrogenase Measurement—

The activity of lactate dehydrogenase (LDH) was measured using the direct spectrophotometric assay using an assay kit from Sigma.

Microinjection of Aβ into the Frontal Cortex of C57/BL6 Mice—

Figure 9A:
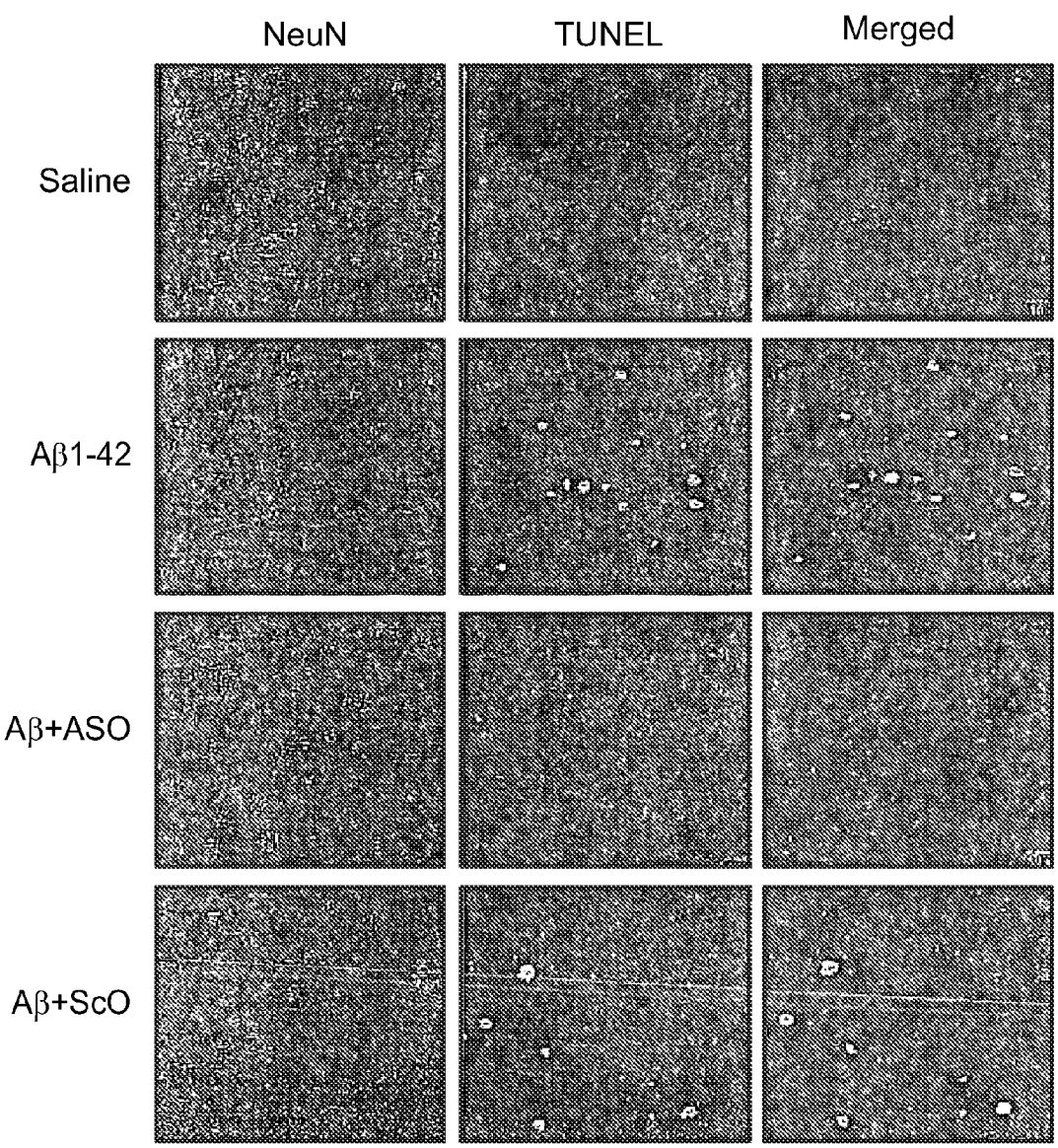
FIGS. 9A-9B photographically and graphically illustrate that antisense oligonucleotides against N-SMase protect neurons from fibrillar Aβ toxicity in in vivo in the cortex of C57BL/6 mice.

C57/BL6 mice (10-12 week old) were anesthetized with ketamine and xylazine and underwent cortical operations in a kopf small animal stereotaxic instrument (David Kopf, CA). Briefly, the animal was mounted in a stereotaxic frame on a heating blanket. Body temperature was maintained at 37+0.5° C. during the time of surgery. A midsagittal incision was made to expose the cranium and a hole <0.5 mm in diameter was drilled with a dental drill over the frontal cortex according to the following coordinates: 1.5 mm anterior to bregma, 1.5 mm lateral to bregma and 1 mm ventral (FIG. 9A). One microgram of either Aβ1-42 or Aβ42-1 in 2 μl of saline was injected using a 5 μl syringe (Hamilton, Reno, Nev.) over a period of 3 min, and the needle was held in place for another 2 min before withdrawing it from the skull to prevent reflux up the needle tract. Similarly, control mice received 2 μl of saline. During antisense treatment, 1 μg of either ASO or ScO against N-SMase dissolved in 2 μl saline was stereotaxically injected into the frontal cortex of C57/BL6 mice. After 24 h of ASO/ScO microinjection, 1 μg of fibrillar Aβ1-42 in 2 μl volume was again microinjected at the same site as described above. The incision was closed with surgical staples and covered with a mixture of Bacitracin and Hurricane (20% benzocaine).

Semi-Quantitative Reverse Transcriptase-Coupled Polymerase Chain Reaction (RT-PCR)—

Total RNA was isolated from human primary astrocytes using RNA-Easy Qiagen kit following manufactures protocol. To remove any contaminating genomic DNA, total RNA was digested with DNase. Semi-quantitative RT-PCR was carried out as described earlier using oligo (dT) 12-18 as primer and MMLV reverse transcriptase (Clontech) in a 20-μl reaction mixture. The resulting cDNA was appropriately diluted, and diluted cDNA was amplified using Titanium Taq polymerase and the following primers for human proinflammatory genes:

```
TNF-a (378 bp),
                                    (SEQ. ID. NO.: 1)
Sense,
5'- CTG AGT CGG TCA CCC TTC TCC AGC
T-3'
                                    (SEQ. ID. NO.: 2)
Antisense,
5-CCC GAG TGA CAA GCC TGT AGC CCA T-3'

IL-Iβ (263 bp):
                                    (SEQ. ID. NO.: 3)
Sense,
5'-GGA TAT GGA GCA ACA AGT GG-3'

(SEQ. ID. NO.: 4)
Antisense,
5-ATG TAC CAG TTG GGG AAC T -3'

IL-6 (236 bp):
                                    (SEQ. ID. NO.: 5)
Sense,
5 -TTT TGG AGT TTG AGG TAT ACC TAG- 3

(SEQ. ID. NO.: 6)
Antisense,
5- GCT GCG CAG AAT GAG ATG AGT TGT- 3 iNOS (368 bp):
                                    (SEQ. ID. NO.: 7)
Sense,
5- CTG CAG ACA CGT GCG TTA CTC CAC
C -3'
                                    (SEQ. ID. NO.: 8)
Antisense,
5'- GCA GGG CGT ACC ACT TTA GCT CCA G -3'

GAPDH (300 bp):
                                    (SEQ. ID. NO.: 9)
Sense,
5'- GGT GAA GGT CGG AGT CAA CG -3'

(SEQ. ID. NO.: 10)
Antisense,
5'- GTG AAG ACG CCA GTG GAC TC -3'
```

Amplified products were electrophoresed on a 1.8% agarose gels and visualized by ethidium bromide staining. Message for the GAPDH (glyceraldehyde-3-phosphate dehydrogenase) gene was used to ascertain that an equivalent amount of cDNA was synthesized from different samples.

Quantitative Real-Time PCR Analysis—

It was performed using the ABI-Prism7700 sequence detection system (Applied Biosystems, Foster City, Calif.) using TaqMan Universal Master Mix and optimized concentrations of FAM-labeled probe, forward and reverse primers (Applied Biosystems) as described earlier. The mRNA expression of iNOS was normalized to the label of GAPDH mRNA. Data were processed by the ABI Sequence Detection System 1.6 software and analyzed by ANOVA.

Electrophoretic Mobility Shift Assay (EMSA)—

Nuclear extracts were prepared and EMSA was carried out as described previously with some modifications. Briefly, IRDye™ infrared dye end-labeled oligonucleotides containing the consensus binding sequence for NF-κB (5'-AGT TGA GGG GAG TTT CCC AGG C-3') (SEQ. ID. NO.: 11) were purchased from Licor Biosciences. Six-micrograms of nuclear extract was incubated with binding buffer and with IR-labeled probe for 20 min. Subsequently, samples were separated on a 6% polyacrylamide gel in 0.25×TBE buffer (Tris borate-EDTA) and analyzed by Odyssey Infrared Imaging System (LI-COR Biosciences).

Transmission Electron Microscopy (TEM) Sample Preparation—

Aliquots of sample (5 μl) were pipetted on to the surface of carbon-coated electron microscope grids and adsorbed for 2 min at room temperature. After rinsing with 20 μl of sterile deionized water, 5 μl of 1% (w/v) uranyl acetate was added for 15-20 s. Grids were then blotted dry and examined under JEOL JEM-1220 transmission microscope.

Statistical Analysis—

All values were expressed as means+SD of three independent experiments. Statistical differences between means were calculated by the Student's i-test. A p-value of less than 0.05 ($p<0.05$) was considered statistically significant.

Results

Activated Primary Human Astroglia Induce Apoptosis and Cell Death in Primary Human Neurons:

Recently, glial activation has been attributed to be one of the major causes of neuronal loss in several neurodegenerative disorders, including AD. However, mechanisms by which activated glia facilitate neuronal loss are poorly understood. Due to the facts that fibrillar Aβ1-42 peptide is an important pathogenic molecule for AD and that astrocytes are major glial cells in the CNS, the effect of Aβ1-42-activated primary human astrocytes on the survival of primary human neurons was examined. To potentiate the neurotoxic effect of Aβ peptides and to simulate the in vivo situation, astrocytes were stimulated with a combination of fibrillar Aβ1-42 and IL-Iβ. Further, reports from our lab and elsewhere have reported a critical role of IL-1β in the expression of iNOS and the production of NO in primary human astrocytes either alone or in combination with other neurotoxins.

Primary human astrocytes were stimulated with 1 μM fibrillar Aβ, 10 ng/ml IL-Iβ or the combination of the two for 24 hr under serum free conditions followed by addition of activated astrocytes on neurons under trans-well setting where activated astroglia being present on inserts were not in direct contact with neurons cultured on 12-well plates. Under this experimental setting, cytotoxic mediators released from activated astrocytes were able to reach human neurons. After 6 h of challenge of neurons by activated astrocytes, apoptosis and cell death were analyzed in neurons by TUNEL. TdT-mediated labeling of DNA fragments was not observed in control unchallenged neurons (FIG. IA—top panel & 1C). Unstimulated human astrocytes were also unable to induce any apoptosis in human neurons (FIG. IA—middle panel & 1C). Although either fibrillar Aβ- or IL-Iβ-activated astrocytes induced some apoptosis in neurons, astrocytes stimulated by the combination of Aβ and IL-1β was much more potent than either Aβ- or IL-Iβ-stimulated astrocytes in inducing neuronal apoptosis (FIG. I, FIG. IB—bottom panel & ID). In another parallel set of experiments, the effect of unstimulated and (Aβ+IL-1β-stimulated astrocytes on neuronal structure was examined after 18 h of challenge by MAP-2 immunofluorescence. Control unchallenged neurons stained MAP-2 uniformly and exhibited neuronal processes (FIG. 1C; top panel). Unstimulated astrocytes were not able to alter MAP-2 immunoreactivity and neuronal morphology (FIG. 1C; middle panel). On the other hand, loss of neuronal processing and marked decrease in MAP-2 immunoreactivity after challenge by Aβ-stimulated astrocytes was observed (FIG. 1C; bottom panel).

Activated primary human astroglia induce the activation of neutral sphingomyelinase (N-SMase) and the production of ceramide in primary human neurons: Next, to gain insight into molecular mechanisms involved in activated astroglia-induced apoptosis and death of primary human neurons, the role of ceramide, a well known inducer of apoptosis, was explored. Neurons were challenged with (Aβ+IL-1β-activated astrocytes, and the level of ceramide was measured in neurons at different time periods using the DAG kinase assay. Within 30 min of challenge, activated astroglia were able to induce the level of ceramide by about 2-fold, and with further increase in duration of insult, the level of ceramide increased markedly (FIG. IE). After 12 h of insult, about 8-fold increase in ceramide production was recorded in human neurons (FIG. IE). Because DAG kinase phosphorylates both DAG and ceramide using [γ-$^{32}$P]ATP as a substrate, both lipids can be quantified in the same assay. Although the DAG content was much higher than the ceramide content, in contrast to a time-dependent increase in the production of ceramide, the level of DAG in insulted neurons remained almost same at different time points of astroglial insult (data not shown).

Next to determine whether Aβ-stimulated astroglia induced the production of ceramide in neurons through the activation of SMases, activities of N-SMase and A-SMase in neurons before and after challenge with activated astroglia were measured. As shown in FIG. IF, a marked induction of N-SMase activity was observed in primary human neurons in response to activated astrocytes in a trans-well setting. Significant increase in N-SMase activity in human neurons was detected as early as 30 min of challenge with activated astrocytes and the maximum induction (~3.5-fold) was observed at 1 h of challenge (FIG. IF). In contrast, Aβ-activated astrocytes were able to increase the activity of A-SMase by about 70% in neurons (FIG. IF) under similar experimental setting. These results suggest that Aβ-activated human astroglia induce the level of ceramide in human neurons through SMase-mediated catabolism of sphingomyelin.

Activated Primary Human Astroglia Induce Apoptosis and Cell Death in Primary Human Neurons Via N-SMase:

Next, an examination of the role of N-SMase and A-SMase in activated astroglia-mediated neuronal apoptosis was carried out. Because antisense oligonucleotides (ASOs) are powerful tools to inhibit target gene expression in non-diving cells in a sequence specific manner, ASOs to knockdown N-SMase and A-SMase in primary human neurons was used. As reported in our earlier studies, following ASOs and scrambled oligonucleotides (ScO) were used to knockdown these molecules.

```
N-SMase:
                            (SEQ. ID. NO.: 12)
ASO:      5'- CAGCGAGCCCGTCCACCAGCC -3'

(SEQ. ID. NO.: 13)
ScO:      5'- CACGCGTCCGACGCCGCACGA -3'

A-SMase:
                            (SEQ. ID. NO.: 14)
ASO:      5'- GACATCTCGGAGCCGGGGCA -3'

(SEQ. ID. NO.: 15)
ScO:      5'- GGAAACCCGGTTAGGCCCGG -3'
```

Because these ASOs have become a very critical part of our study, the efficacy of N-SMase and A-SMase ASOs in inhibiting the protein expression of N-SMase and A-SMase was checked by western blot. As evident from FIG. 2A, ASO against N-SMase effectively inhibited the level of N-SMase, but not A-SMase, protein. Similarly, ASO against A-SMase suppressed the level of A-SMase, but not N-SMase, protein (FIG. 2B). On the other hand, ScO had no effect on the protein level of either N-SMase or A-SMase (FIGS. 2A&B) suggesting the specificity of the effect. Next, the effect of antisense knockdown of neuronal N-SMase and/or A-SMase on activated glia-induced neuronal apoptosis by TUNEL was investigated. As evident from FIG. 2C, control neurons showed a very few apoptotic bodies after 6 h of incubation with unstimulated astrocytes in neuron-astrocyte trans-well culture, but exhibited a marked increase in apoptosis in response to activated astrocytes (FIGS. 2C & 2D). However, ASO, but not ScO, against neuronal N-SMase markedly protected neurons from the insult of activated astrocytes (FIGS. 2C & 2D). However, under similar experimental condition, ASO against A-SMase failed to rescue neurons (data not shown). To further strengthen these results, neuronal death by MTT and LDH was monitored. As evidenced by a decrease In MTT metabolism, activated astroglia reduced neuronal viability (FIG. 2E). Consistent to TUNEL data, ASO against N-SMase, but not A-SMase, effectively prevented activated astroglia-mediated loss of MTT metabolism in human neurons (FIG. 2E). Similarly, treatment of human neurons with ASO against N-SMase, but not A-SMase, resulted in the significant reduction in LDH release from neurons (FIG. 2E) in response to insult from activated astrocytes. On the other hand, ScO against N-SMase showed no effect on cell viability under similar experimental settings (FIG. 2E).

To confirm these results further, specific pharmacological inhibitors of N-SMase and A-SMase were Fused. While GW4869 is a specific synthetic inhibitor of N-SMase imipramine has been shown to block the activity of A-SMase, but not N-SMase. At first, the specificity of these two inhibitors in the experimental setting was checked. Activated human astrocytes induced the activation of both N-SMase and A-SMase in human neurons (FIG. 2). While GW4869 strongly suppressed the activity of N-SMase, but not A-SMase, imipramine inhibited the activity of A-SMase, but not N-SMase, in activated astroglia-insulted human neurons (FIG. 2) suggesting the specificity of these compounds. As evident from MTT metabolism in FIG. 2F and LDH release in FIG. 2G, pretreatment of neurons with GW4869, but not imipramine, was able to protect human neurons from activated astroglia-induced cell death. These findings suggest that Aβ-activated human astrocytes induce apoptosis and cell death in human neurons via N-SMase.

Identification of an Astroglial Soluble Mediator, which is Responsible for Neuronal Death:

In AD, an inflammatory response characterized by glial activation is seen surrounding the plaque region. Results described above clearly suggest that once astroglia become activated, soluble gliotoxins released from these glial cells destroy human neurons via N-SMase. In an effort to identify such an astrogliotoxin that could be responsible for neuronal death, at first, the possibility that ceramide was released from activated astrocytes to act intercellularly on neurons as a pro-apoptotic signal was considered. Primary astrocytes were activated by the combination of Aβ and IL-Iβ for different time periods followed by assay of ceramide in conditioned media. As evident from FIG. 3A, there was no increase in extracellular ceramide. However, as expected, the level of intracellular ceramide increased significantly under the same experimental condition (FIG. 3B). These results rule out the involvement of extracellular ceramide as a soluble mediator for neuronal death in our trans-well culture model. Because activated astroglia also release nitric oxide (NO), a multifunctional molecule, next, any possible role of nitric oxide (NO) in neuronal death was investigated. Interestingly, pretreatment of neurons with PTIO (a scavenger of NO) reduced the ability of activated astrocytes to induce the activation of N-SMase (FIG. 3A), decrease MTT metabolism (FIG. 3B) and increase the release of LDH (FIG. 3C) identifying NO as a possible astroglial soluble mediator for neuronal death. Although reactive oxygen species are known to activate N-SMase, it was not known whether NO could do the same. Whether NO alone was sufficient for the activation of N-SMase in neurons was investigated. As evident from FIG. 3, DETA-NONOate, a NO donor, alone markedly induced the activation of N-SMase (FIG. 3D), but not A-SMase (FIG. 3E), in neurons.

Activation of Human Astrocytes is Dependant on N-SMase.

Although soluble gliotoxins released from activated human astrocytes destroy human neurons via N-SMase, it is not known whether N-SMase is also involved during the activation of glial cells. Upon activation, glial cells release various proinflammatory molecules. Earlier it was found that among various stimuli (LPS, TNF-α, IL-Iβ, and IFN-γ) tested, only IL-Iβ is capable of inducing the production of NO in human fetal astroglia. It is evident from FIG. 4A that fibrillar Aβ1-42 alone was also capable of inducing the production of NO in primary human astroglia at a comparable level to that by IL-Iβ. However, the combination of IL-Iβ and Aβ induced the production of NO at a level higher than that found by these stimuli alone (FIG. 4A). Therefore, this combination was used to stimulate primary human astroglia. Next the effect of antisense knockdown of N-SMase on the production of NO was investigated. It is clear from FIG. 4A that antisense knockdown of N-SMase, but not A-SMase, markedly abrogated (Aβ+IL-Iβ)-induced production of NO in human astroglia. On the other hand, scrambled oligonucleotides (ScO) had no effect on NO production suggesting the specificity of the effect. Next, the effect of chemical knockdown of N-SMase on astroglial production of NO was examined. While GW4869, a specific inhibitor of N-SMase, markedly suppressed (Aβ+IL-Iβ)-induced production of NO, A-SMase inhibitor imipramine showed no effect on NO production (FIG. 4B). These results suggest that N-SMase, but not A-SMase, is involved in the production of NO from activated human astroglia.

Next to confirm these results from another angle; the RNA expression of iNOS in activated astrocytes was examined. As expected, the combination of Aβ and IL-Iβ induced the expression of iNOS mRNA (FIG. 4C). Consistent to the effect of N-SMase ASO on the production of NO, antisense knockdown of N-SMase, but not A-SMase, strongly inhibited the expression of iNOS mRNA while ScOs had no impact on (Aβ+IL-Iβ)-induced expression of iNOS (FIG. 4C). Realtime PCR data (FIG. 4D) also corroborated these findings. In addition to expressing iNOS, activated astrocytes are also known to express various proinflammatory cytokines. Consistently, (Aβ+IL-Iβ) induced the expression of TNF-α, IL-1β and IL-6 mRNAs in human astroglia (FIG. 4E). However, similar to the effect of antisense knockdown of N-SMase on the expression of iNOS mRNA, ASO against N-SMase, but not A-SMase, abrogated the ability of (Aβ+IL-Iβ) to induce the expression of TNF-α, IL-1β and IL-6 mRNAs (FIG. 4E). Taken together, these results suggest that the expression of proinflammatory molecules in activated human astroglia depends on N-SMase, but not A-SMase.

Oligomeric Aβ1-42 Peptides Activate Primary Human Astrocytes.

Figure 5A:
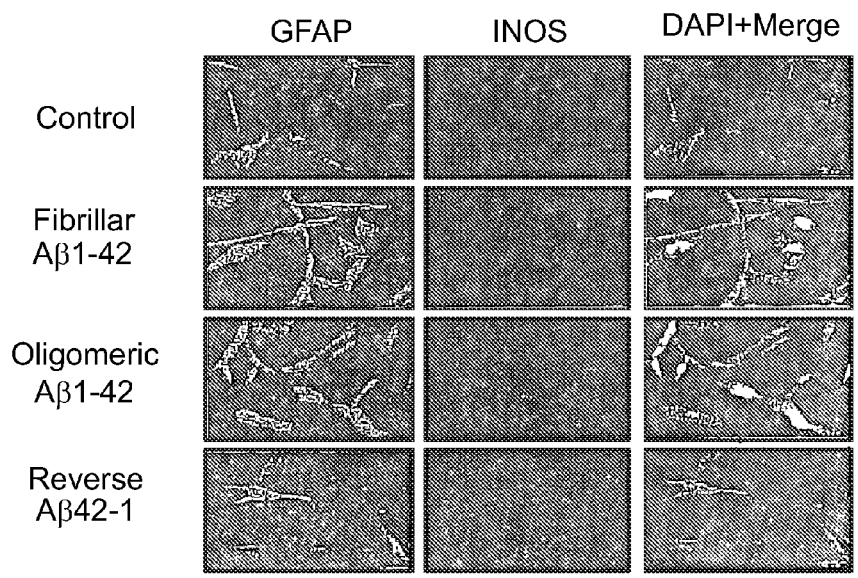
FIGS. 5A-5C illustrate photographically and graphically that oligomeric Aβi$^\wedge_2$-activated astrocytes induce apoptosis in neurons via N-SMase in neuron-astrocyte transwell cultures.

Although fibrillar Aβ peptides are used to mimic activated astroglia-induced neuronal death, recent studies have shown that in addition to fibrillar Aβ, oligomeric Aβ is also capable of inducing profound inflammatory response in glial cells. Therefore, whether oligomeric Aβ1-42 induced the activation of human astroglia and whether oligomeric Aβ-activated astroglia also kill neurons via N-SMase. As expected, fibrillar Aβ induced the expression of iNOS protein and increased the level of GFAP in human astrocytes (FIG. 5A) was investigated. Similarly, oligomeric Aβ also induced iNOS and upregulated GFAP in astrocytes (FIG. 5A). These results are specific as reverse Aβ42-1 peptides did not have any effect on astroglial GFAP and iNOS (FIG. 5A). Therefore, next the effect of oligomeric Aβ-activated astrocytes on the apoptosis of neurons was examined. Similar to fibrillar Aβ-activated astrocytes, oligomeric Aβ-activated astrocytes also markedly induced apoptosis of human neurons (FIGS. 5B&C) and this effect was blocked by antisense knockdown of N-SMase (FIGS. 5B&C) suggesting that oligomeric Aβ-activated astrocytes also kill neurons via N-SMase.

Activation of NF-κB in Primary Human Astrocytes Also Depends on N-SMase.

Among various transcription factors that are required for the transcription of proinflammatory molecules, NF-κB is a key transcription factor involved in the transcription of almost all proinflammatory molecules. Therefore, to understand the basis of suppression of proinflammatory molecules by inhibition of N-SMase, whether the activation of NF-κB in Aβ-stimulated astroglia was also regulated by N-SMase. Activation of NF-κB was monitored by DNA binding activity of NF-κB was examined. DNA binding activity of NF-κB was evaluated by the formation of a distinct and specific complex in a gel shift DNA binding assay. Treatment of primary human astroglia with (Aβ+IL-Iβ) resulted in the induction of DNA binding activity of NF-κB (FIG. 6A). This gel shift assay detected a specific band in response to (Aβ+Ii-Iβ) (FIG. 6) that was competed off by an unlabeled probe (data not shown) suggesting that (Aβ+IL-1β) induces the DNA-binding activity of NF-κB. However, ASO against N-SMase, but not A-SMase, suppressed (AP+IL-iP)-induced DNA-binding activity of NF-κB (FIG. 6A). On the other hand, under similar condition, ScO had no effect on the DNA-binding activity of NF-κB (FIG. 6A). To confirm these results further, chemical inhibitors of N-SMase and A-SMase reused. Consistent to antisense results, N-SMase inhibitor GW4869, but not ASMase inhibitor imipramine, markedly suppressed (Aβ+IL-ˆ-induced DNA-binding activity of NF-κB (FIGS. 6B & 6C). These results clearly indicate that the activation of NF-κB in human astrocytes also depends on N-SMase, but not A-SMase.

Fibrillar Aβ1-42 peptides induce the activation of N-SMase and the production of ceramide in vivo in the cortex of male C57/BL6 mice: Using various approaches, the studies presented above demonstrate that fibrillar Aβ-activated astroglia kill neurons via N-SMase and that fibrillar Aβ also activate astroglia via N-SMase. Next to address if these findings could be reproduced in vivo in the cortex of mice, fibrillar Aβ1-42 peptides were microinjected into the cortex of male C57/BL6 mice (10-12 week old) (FIG. 7A). First, Aβ peptides were able to induce the activation of N-SMase and the production of ceramide in vivo in the cortex was examined. As evident from FIG. 7B, microinjection of Aβ1-42 peptides led to marked increase in the activation of N-SMase compared to saline microinjection. More than 3 fold increase in the activity of N-SMase was observed at 6 h of microinjection and it increased further at 12 h (FIG. 7B). However, activity of N-SMase decreased at 24 h of microinjection (FIG. 7B). In contrast, reverse peptides (Aβ42-1) were unable to increase the activity of N-SMase in vivo in the cortex as compared to saline microinjection (FIG. 7B). While after 12 h of microinjection, Aβ1-42 increased the activity of N-SMase by more than 300% compared to saline, Aβ42-1 remained unable to increase its activity significantly at the same time point (FIG.

7B). However, under same experimental setting, microinjection of saline, Aβ1-42 or Aβ42-1 was unable to increase the activity of A-SMase significantly in the cortex (FIG. 7C). Then the level of ceramide in the cortex was monitored. Fibrillar Aβ1-42 peptides caused about 3-fold increase in the ceramide level after 6 h and about 4-fold increase in the ceramide level after 12 h as compared to about 30% increase in ceramide level in saline-microinjected cortex at 6 h (FIG. 7D). Taken together, these findings suggest that fibrillar Aβ1-42 peptides induce the generation of ceramide in vivo in the cortex and that ceramide production is due to the activation of N-SMase, but not A-SMase.

Antisense Knockdown of N-SMase Inhibit Fibrillar Aβ-Mediated Astrogliosis In Vivo in the Cortex of C57/BL6 Mice.

At first, efficacy and specificity of ASO against mouse N-SMase (mN-SMase) in vivo in the cortex was examined. Sequences of ASO and ScO against mN-SMase were:

```
                                          (SEQ. ID. NO.: 16)
    ASO, 5'-CAG CGA GCC GGT CCA CCA GCC-3'

(SEQ. ID. NO.: 16)
    ScO, 5'-CAC GCG TCC GAC GCC GCA CGA-3'
```

It is clearly evident from FIG. 4A that fibrillar Aβ1-42 increased the activity of N-SMase in vivo in the cortex by more than 4-fold as compared to saline. However, pre-microinjection of mN-SMase ASO, but not ScO, was capable of suppressing AβI-42-induced activation of N-SMase in vivo in the cortex (FIG. 4A). It is also observed about 35% increase in the activity of A-SMase after Aβ microinjection (FIG. 4B). However, either mN-SMase ASO or mN-SMase ScO did not influence the activity of A-SMase in fibrillar Aβ-microinjected cortex (FIG. 4B).

Glial activation and neuronal apoptosis are two hallmarks of AD. Whether fibrillar Aβ1-42 peptides were capable of inducing glial activation and neuronal apoptosis in vivo in the cortex was investigated. To understand if both are occurring simultaneously or the one is preceding the other in fibrillar AβI-42-insulted cortex, glial expression of iNOS and neuronal TUNEL bodies in cortical sections after 6 h and 24 h of microinjection was examined. Astroglia are the major cell type in the brain and increase in glial fibrillary acidic protein (GFAP) expression represents an important way to monitor astroglial activation. Upon activation, astrocytes express iNOS and produce NO and earlier it was demonstrated that NO plays a critical role in the upregulation of GFAP in astroglia. Similarly, activated microglia also express considerable amount of iNOS and it was demonstrated that NO is an important factor in increasing microglial surface markers required for gliosis. Therefore, the expression of iNOS in both GFAP- and CDIIb-positive cells in cortical sections was monitored. Fibrillar Aβ1-42 peptides induced the expression of iNOS in GFAP-positive astrocytes and CD1 Ib-positive microglia within 6 h of microinjection (data not shown). However, fibrillar Aβ peptides were unable to induce any apoptosis in neurons (NeuN-positive cells) within this time period (data not shown). On the other hand, at 24 h of microinjection, both glial expression of iNOS and neuronal apoptosis were observed (data not shown). These results clearly suggest that in Aβ-microinjected model, glial activation is followed by neuronal apoptosis.

Figures 8A, 8B:
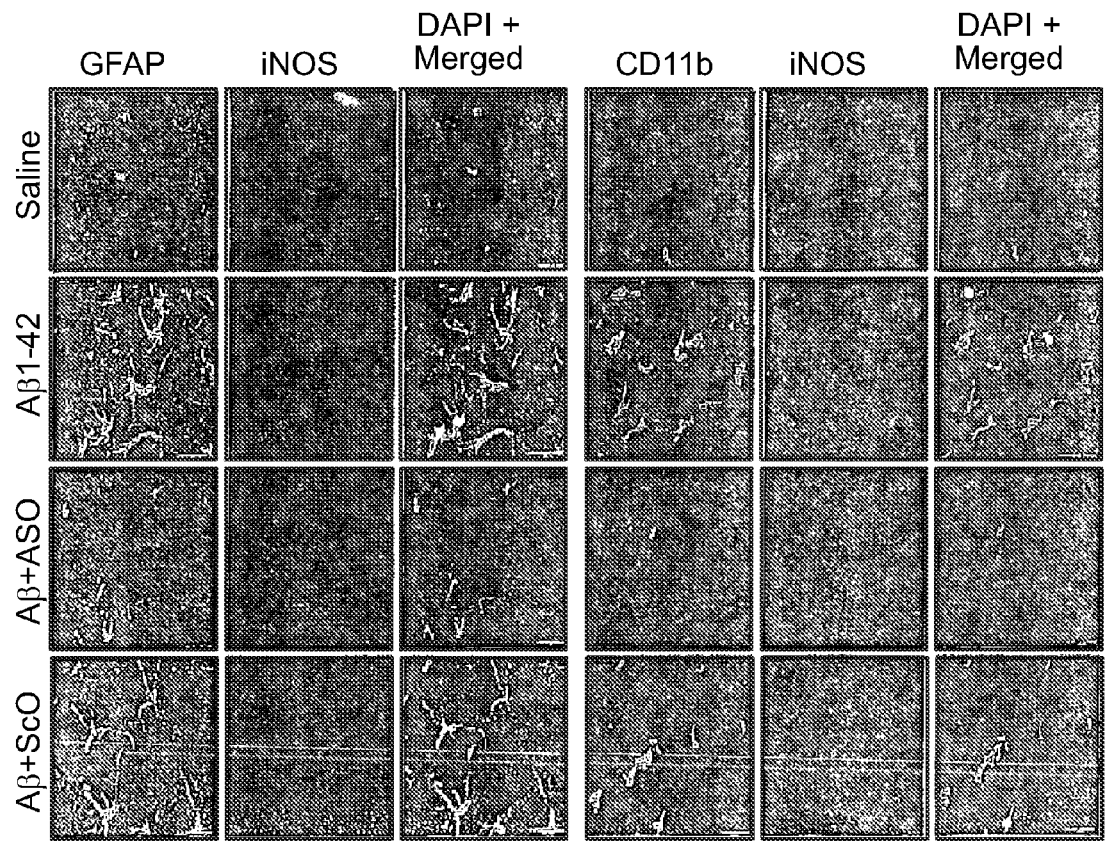
FIGS. 8A-8C photographically and graphically illustrate that antisense knockdown of N-SMase attenuates the activation of astroglia and microglia and reduces the expression of iNOS in vivo in the cortex of C57BL/6 mice.

Therefore, first an investigation of the effect of N-SMase ASO on glial activation was carried out. As evident from FIG. 8A, the level of iNOS was almost undetectable and the level of GFAP was also very low in saline-microinjected mice. On the other hand, marked increase in the expression of iNOS and GFAP was observed in Aβ-injected mice and many iNOS signals co-localized with GFAP-positive astroglia after both 6 h (FIG. 8A) and 24 h (data not shown) of microinjection. Similarly, Aβ microinjection also induced microglial activation as evidenced from increased iNOS staining in CDI Ib-positive microglia after 6 h (FIG. 8A) and 24 h (data not shown) of microinjection. However, antisense knockdown of N-SMase dramatically reduced the expression of iNOS, GFAP and CDI Ib in vivo in the cortex of Aβ-microinjected mice at both 6 h and 24 h of microinjection. On the other hand, as expected, N-SMase ScO had no effect on the expression of iNOS, GFAP and CD1 Ib (FIG. 8). Because there was no neuronal apoptosis in vivo in the cortex after 6 h of microinjection, our results clearly suggest that knockdown of N-SMase is capable of abrogating the inflammatory response in glial cells without involving neuronal apoptosis.

Figure 9B:
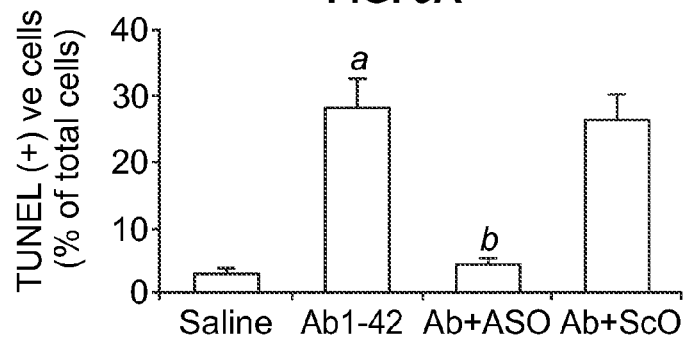

Antisense Knockdown of N-SMase Protects Neurons from Aβ Toxicity In Vivo in the Cortex of C57/BL6 Mice:

Next, an investigation of whether fibrillar Aβ1-42 peptides induced neuronal apoptosis in vivo in the cortex was carried out. Cortical sections were double-labeled for TUNEL and NeuN. As evident from FIG. 9, fibrillar Aβ1-42 markedly induced the apoptotic death of neurons in vivo in the cortex as evidenced by the increase in TUNEL signal in NeuN-positive cells. Whether fibrillar Aβ also induced apoptosis in other three cell types in the cortex was investigated. In contrast to marked apoptosis of neurons, no apoptosis in either GFAP-positive astroglia or Ibal-positive microglia was observed (data not shown). However, TUNEL bodies co-localized with 04-positive oligodendroglia and oligodendroglial progenitors (data not shown). This is consistent with the finding of Lee et al that Aβ peptides induce oligodendroglial apoptosis. Next, whether antisense knockdown of mN-SMase was capable of protecting neurons in vivo in the cortex from Aβ toxicity was investigated. As evident from FIGS. 9A & 9B, the increase in the apoptotic death in vivo in the cortex was blocked by mN-SMase ASO. On the other hand, mN-SMase ScO did not ameliorate cell death in Aβ injected mice under similar experimental conditions suggesting the specificity of the protective effect (FIG. 9).

Discussion

Although the disease mechanisms that cause AD are poorly understood, recent studies strongly support the role of inflammation in neurodegeneration in this disease. First, early intervention with nonsteroidal anti-inflammatory drugs slows disease incidence. Second, significant astroglial and microglial activation occurs in close proximity to neuritic plaques containing Aβ. Third, over-expression of astrocytic S100B leads to brain inflammation and exacerbation of Alzheimer's disease pathology in a mouse model of the disease. Fourth, the concentration of $NO_2^-$ (nitrite), a metabolite of NO, increases in the cerebrospinal fluid (CSF) of patients with AD compared to age-matched controls. It has been shown that glial cells in the cortex from postmortem AD samples express considerable amounts of inducible nitric oxide synthase (iNOS), whereas those from age-matched controls do not. Fifth, a variety of proinflammatory cytokines including TNF-a, IL-Iβ, IL-6, eicosanoids, and other immune neurotoxins are found in either CSF or affected brain regions in AD. Sixth, concentration of various chemokines, such as IL-8, MCP-1 and IP-10 increases in CSF of patients with mild cognitive impairment (MCI) and AD as compared to age-matched control. Seventh, NF-κB is considered as a proinflammatory transcription factor because of its involvement in the transcription of almost all proinflammatory molecules. It has been found that in AD brains, NF-κB immunoreactivity is higher in astrocytes surrounding the plague region. Eighth, in addition to releasing nitric oxide, proinflammatory cytokines and chemokines, activated glia also produce reactive oxygen species and eicosanoids capable of damaging neurons. Taken together, these studies demonstrate the utmost importance of unraveling mechanisms of glial activation and activated glia-mediated neuronal death for providing significant insight into the pathophysiology of AD and developing treatment paradigms.

Intracellular signaling mechanisms involved in Aβ-induced glial activation are poorly understood. Recent studies have shown that Aβ activates three subtypes of mitogen-activated protein kinases (MAPK) in glial cells, such as extracellular signal-regulated kinase (ERK), c-Jun N-terminal kinase (JNK) and p38 kinase. Out of the three MAPKs, p38 and JNK, but not ERK1/2, have been shown to play an important role in mediating the activation of glia. Here it was found that fibrillar Aβ1-42 peptides activate human astroglia via neutral sphingomyelinase (N-SMase). First, knockdown of N-SMase by either chemical inhibitor or antisense oligonucleotides suppresses Aβ-induced production of nitrite and the expression of iNOS and proinflammatory cytokines (TNF-α, IL-Iβ and IL-6) in primary human astrocytes. On the other hand, knockdown of A-SMase had no effect on Aβ-induced activation of human astroglia suggesting the specificity of the effect. Earlier studies have also shown the involvement of N-SMase in the induction and/or stimulation of iNOS in C6 rat glioma cells or oligodendrocytes. Second, inhibition of N-SMase, but not A-SMase, attenuated the activation of NF-κB in fibrillar Aβ-stimulated human astrocytes. Our result is in direct contrast with earlier reports where TNF-α has been shown to induce the activation of NF-KB via A-SMase. While TNF-α requires TNFR1-A-SMase pathway for the activation of NF-KB, fibrillar Aβ couples different receptors (RAGE, scavenger receptor etc), which may prefer N-SMase for transducing signals for the activation of NF-κB in human astroglia. Third, antisense knockdown of N-SMase also inhibited the expression of iNOS in vivo in fibrillar Aβ-intoxicated mouse cortex. Earlier it was demonstrated that fibrillar Aβ kills human neurons via activation of N-SMase. Here it is demonstrated that fibrillar Aβ activates human astroglia in culture and mouse astroglia in vivo in the cortex via N-SMase. Earlier, it has been shown that ceramide stimulates the activation of NF-κB and the expression of iNOS in primary rat astrocytes. Recently it was demonstrated that NO is an important signal for the upregulation of GFAP in astrocytes. Therefore, it appears that the activation of N-SMase-ceramide pathway is one of the earlier events for the initiation of NF-κB-iNOS-NO-GFAP pathway, which ultimately culminates into astroglial activation and astrogliosis. Here it was also delineated a nice feedback regulation of N-SMase by NO as well. Although proinflammatory cytokines (TNF-α and IL-Iβ) and reactive oxygen species are known to induce N-SMase, it was not known whether NO is capable of activating N-SMase. Our results suggest that NO produced from activated glial cells could activate N-SMase on its own in neurons.

Once glial cells are activated, in addition to producing NO, these activated cells produce diverse set of molecules, such as proinflammatory cytokines, proinflammatory chemokines, reactive oxygen species, and arachidonic acid, which could damage neurons on their own. Therefore, it is important to identify a common molecule where various signaling pathways emanating from different neurotoxic molecules converge. Several lines of evidence presented in this manuscript clearly indicate that Aβ-activated primary human astroglia kill primary human neurons via N-SMase. First, in a trans-well setting where astrocytes were not in direct contact with neurons, fibrillar Aβ-activated astroglia induced the activation of N-SMase, the production of ceramide and cell death in neurons. However, antisense knockdown of neuronal N-SMase, but not A-SMase, protected these cells against fibrillar Aβ-activated astroglia as evidenced by decrease in TUNEL positive cells, amelioration in LDH release and restoration of MTT metabolism. Consistently, treatment of neurons with N-SMase inhibitor GW4869, but not A-SMase inhibitor imipramine, also led to protection of neurons from activated astroglia insult. Second, stereotaxic injection of fibrillar Aβ1-42 peptides, but not soluble Aβ42-1 reverse peptides, increased the activity of N-SMase, the production of ceramide and the apoptosis of neurons in mouse cortex. However, antisense knockdown of N-SMase protected cholinergic neurons in vivo in the cortex from fibrillar Aβ toxicity.

Figure 10:
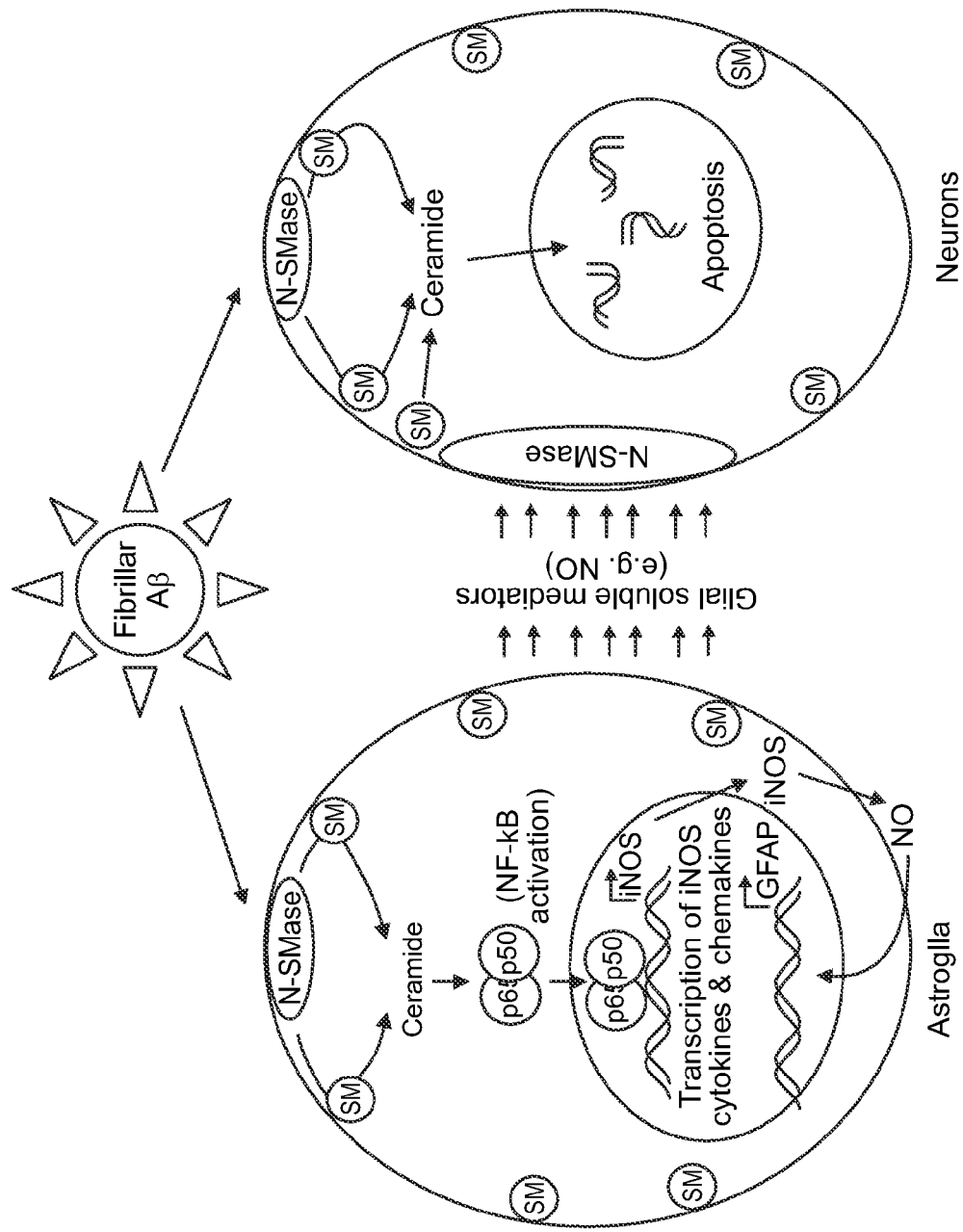
FIG. 10 schematically presents a summary of the research disclosed herein.

In vivo in the brain of AD patients, fibrillar Aβ peptides exert effect on neurons as well as glial cells. Although according to our earlier work, knockdown of N-SMase protects neurons from direct toxic effects of fibrillar Aβ, glial-derived neurotoxic factors may kill neurons independent of N-SMase, thereby limiting the therapeutic potential of inhibitors of N-SMase in AD. Here it is demonstrated that fibrillar Aβ activates glial cells via N-SMase and that N-SMase is also involved in activated glial cell-induced neuronal death (summarized in FIG. 10). These results suggest that N-SMase is the converging point of multiple neurotoxic signaling pathways (FIG. 10). Although the in vitro situation of human fetal neurons and astroglia in culture does not truly resemble the in vivo situation of neurons in the brain of AD patients, our results suggest that specific targeting of N-SMase may be an important therapeutic avenue to halt neuronal damage in AD and other neurodegenerative disorders like Parkinson's disease, multiple sclerosis and Huntington's disease.

INDUSTRIAL APPLICATION

As shown in FIGS. 1A-1F, activated primary human astrocytes induce apoptosis and the activation of neutral sphingomyelinase (N-SMase)-ceramide pathway in primary human neurons in neuron-astrocyte trans-well cultures. In FIG. 1A, the morphology of oligomeric and fibrillar form of Aβ1-42 peptides was examined by transmission electron microscopy. In FIG. IB, Primary human astrocytes seeded in inserts were stimulated with a combination of 1 µM of fibrillar Aβ and 10 ng/ml of IL-Iβ in serum free media. After 24 h, media were removed and inserts with activated astrocytes were placed on coverslips containing primary neurons for 6 h followed by TUNEL. In FIG. 1C, after 18 h of treatment of neurons with activated astrocytes, cells were immunostained with MAP-2. In FIG. ID, TUNEL-positive cells were counted manually in four different images of each of three coverslips by three individuals blinded to the experiment. Values obtained from the control group (1) served as 100%, and data obtained from other two groups i.e. the normal astrocyte-neuron group (2) and the activated astrocytes-neuron group (3) was calculated as percent of control accordingly. Results are mean+S.D. of three different experiments. $^{a}p<0.001$ vs control. Activated astrocytes were placed on human neurons and further incubated for different time intervals. Lipids were extracted from neurons at respective time points, and ceramide levels (FIG. IE) were determined. $^{a}p<0.001$ vs 0 h. Activities of N-SMase and A-SMase (FIG. IF) were assayed in total cell extract of neurons. Control group served as 100%, and data from other groups were expressed as percentage of control. Results are mean+SD of three different experiments. $^{a}p<0.001$ vs 0 h.

FIGS. 2A-2G show that antisense or chemical knockdown of N-SMase, but not A-SMase, protects neurons from Aβ-activated primary human astrocytes in astrocyte-neuron trans-well cultures. Primary human neurons were incubated with antisense (ASO) and scrambled oligonucleotides (ScO) against N-SMase (A) and A-SMase (FIG. 2B). After 48 h, neurons were analyzed for protein expression of N-SMase and A-SMase. In FIG. 2C, primary human astrocytes seeded in inserts were stimulated by the combination of Aβ and IL-1β as described above. After 24 h, media were removed and inserts were washed and placed on neurons that were already pretreated for 40 h with 1 μM of either ASO or ScO against N-SMase and A-SMase. After 6 h of treatment with activated astrocytes, apoptotic events in neurons were detected by TUNEL. In FIG. 2D, TUNEL-positive cells were counted manually in four different images of each of three coverslips by three individuals blinded to the experiment. In FIG. 2E, after 18 h of stimulation, cell viability was examined by the metabolism of MTT and the release of LDH. Activated astrocytes were placed on neurons that were pretreated with different concentrations of GW4869 (GW) and imipramine. Cell viability was checked by MTT (FIG. 2F) and LDH (FIG. 2G). Values obtained from the control group served as 100%, and data obtained in other groups were calculated as percent of control accordingly. Results are mean+S.D. of three different experiments. $^{a}p<0.001$ vs control; $^{b}p<0.001$ vs FAA. FAA, (Fibrilar A+IL-1β)-activated astrocytes.

Figure 3B:
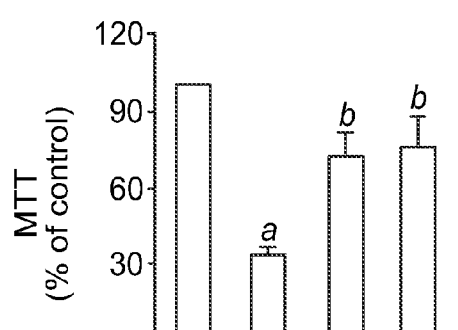
Figure 3C:
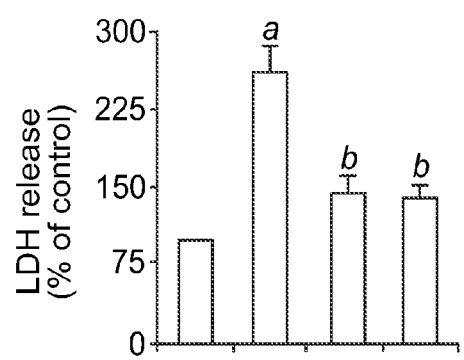
Figure 3D:
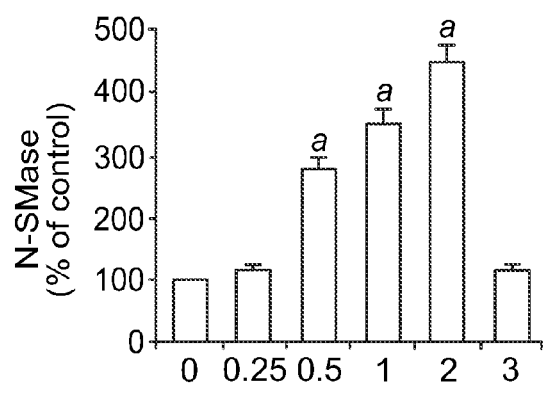
Figure 3E:
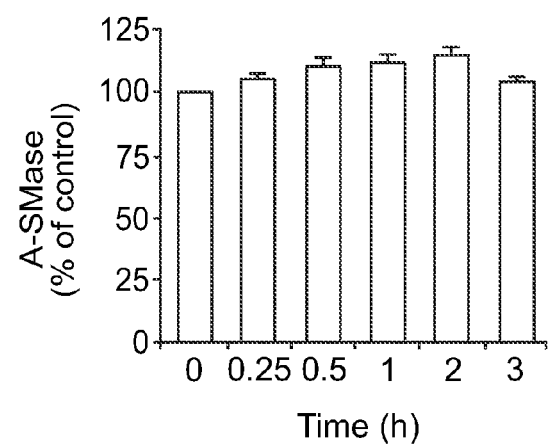

In FIGS. 3A-3E, primary human astrocytes seeded in inserts were stimulated by the combination of Aβ and IL-Iβ as described above. After 24 h, media were removed and inserts were washed and placed on neurons that were pretreated with PTIO for 30 min. In FIG. 3A, after 1 h, activity of N-SMase was measured in total cell extracts of neurons as described above. After 18 h, neuronal viability was examined by the metabolism of MTT (FIG. 3B) and the release of LDH (FIG. 3C). Values obtained from the control group served as 100%, and data obtained in other groups were calculated as percent of control accordingly. Results are mean+S.D. of three different experiments. $^{a}p<0.001$ vs control; $^{b}p<0.001$ vs activated astrocytes. Primary human neurons were treated with 25 μM DETA-NONOate (a NO donor) and at different time points of treatment, activities of N-SMase (FIG. 3D) and A-SMase (FIG. 3E) were monitored. $^{a}p<0.001$ vs control (0 h).

FIGS. 4A-4E show that antisense and chemical knock-down of N-SMase, but not A-SMase, blocks the expression of iNOS and proinflammatory cytokines in (Aβ+IE-Iβ)-activated primary human astrocytes. Cells pretreated with ASO and ScO against N-SMase and A-SMase for 40 h were stimulated with (Aβ+IL-1β) under serum-free condition. After 24 h of stimulation, the concentration of nitrite was measured in supernatants (FIG. 4A) by Griess reagent. In FIG. 4B, cells preincubated with different concentrations of GW4869 and imipramine for 30 min were stimulated as above and nitrite level was measured after 24 h of stimulation. Cells were treated with ASO/ScO for 40 h followed by stimulation with the combination of fibrilar Aβ and IL-Iβ as above. After 6 h, the expression of iNOS mRNA was analyzed by both semi-quantitative RT-PCR (C) and quantitative real-time PCR (FIG. 4D). The expression of TNF-a, IL-6 and IL-Iβ mRNAs were analyzed by semi-quantitative RT-PCR (FIG. 4E). Results are mean±SD of three different experiments. $^{a}p<0.001$ vs control; $^{b}p<0.001$ vs (Aβ+IL-Iβ).

Figure 5B:
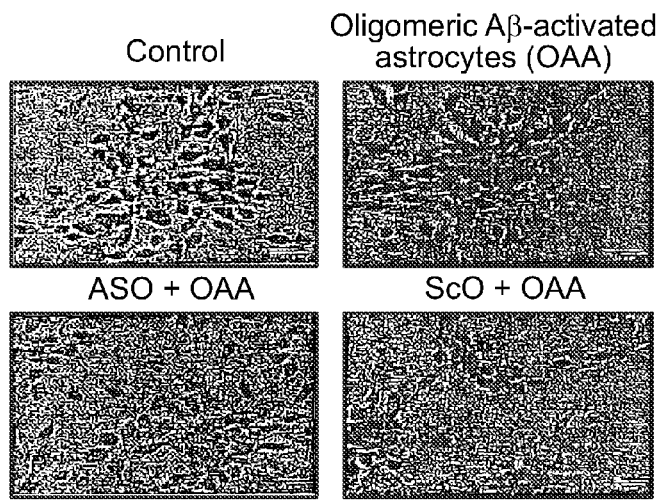
Figure 5C:
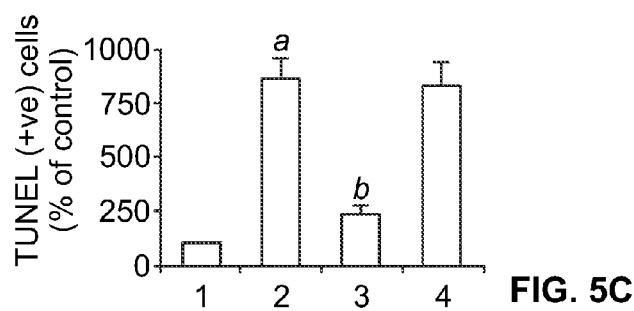

FIGS. 5A-5C show that oligomeric Aβ1-42-activated astrocytes induce apoptosis in neurons via N-SMase in neuron-astrocyte trans-well cultures. In FIG. 5A, primary astrocytes were stimulated with fibrillar Aβ1-42, oligomeric Aβ1-42 and reverse peptide Aβ42-1 for 24 h followed by double-labeling of GFAP and iNOS. In FIG. 5B, primary human astrocytes seeded in inserts were stimulated with a combination of I μM of oligomeric Aβ1-42 and 10 ng/ml of IL-Iβ in serum free media. After 24 h, media were removed and inserts with activated astrocytes were placed on coverslips containing primary neurons that were already pretreated for 40 h with I μM of either ASO or ScO against N-SMase. After 6 h, neuronal apoptosis was monitored by TUNEL. In FIG. 5C, TUNEL-positive cells were counted manually in four different images of each of three coverslips by three individuals blinded to the experiment. Values obtained from the control group (1) served as 100%, and data obtained from other three groups i.e. the oligomeric Aβ-activated astrocytes (OAA) group (2), the ASO-OAA group (3), and the ScO-OAA group (4) was calculated as percent of control accordingly. Results are mean+S.D. of three different experiments. $^{a}p<0.001$ vs control; $^{b}p<0.001$ vs OAA.

FIG. 6A shows that cells treated with I μM of either ASO or ScO against N-SMase and A-SMase for 40 h in complete media were stimulated with (Aβ+IL-1β) under serum-free condition. After I h of stimulation nuclear extracts were prepared and subjected to EMSA for the detection of NF-κB. In the other set of experiments, cells preincubated with different concentrations of GW4869 (FIG. 6B) and imipramine (FIG. 6C) for 30' were stimulated with (Aβ+IL-Iβ) for 1 h followed by EMSA. The upper and lower arrows indicate the induced NF-κB band and the unbound probe, respectively. Results represent three independent experiments.

FIGS. 7A-7D show that fibrillar Aβ1-42 peptides induce the activation of N-SMase and the production of ceramide in vivo in the cortex of C57/BL6 mice. One microgram of either fibrillar Aβ1-42 or reverse Aβ42-1 peptides dissolved in saline was stereotaxically injected into the frontal cortex (FIG. 7A) of C57/BL6 mice. Control mice received saline injection. At indicated time points, cortex was dissected out and divided into two halves—one half for measuring activities of N-SMase (FIG. 7B) and A-SMase (FIG. 7C) and the other for assaying ceramide (FIG. 7D). Control (saline—6 h) group served as 100%, and data from other groups were expressed as percentage of control. Results are mean+SD of five different mice (n=5). $^{a}p<0.05$ vs saline—6 h.

Figure 8C:
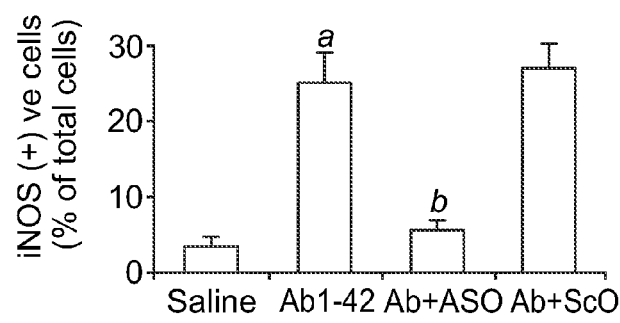

FIGS. 8A-8C show that antisense knockdown of N-SMase attenuates the activation of astroglia and microglia and reduces the expression of iNOS in vivo in the cortex of C57/BL6 mice. One microgram of either ASO or ScO against N-SMase dissolved in 2 μl saline was stereotaxically injected into the frontal cortex of C57/BL6 mice. After 24 h of micro-injection, 1 μg of fibrillar Aβ1-42 in 2 μl volume was again microinjected at the same site. After 6 h of Aβ microinjection, mice were perfused and double immunofluorescence for GFAP (green) and iNOS (red) (FIG. 8A) and CD 11b (green) and iNOS (red) (FIG. 8B) was performed. Five mice (n=5) were used in each group. In FIG. 8C, cells positive for iNOS as well as total DAPI positive cells were counted in three cortical sections (two images per slide) of each of five different mice in an Olympus ΓX81 fluorescence microscope using the MicroSuite™ imaging software. Results are expressed as number of iNOS-positive cells per 100 cells. $^{a}p<0.001$ vs saline; $^{b}p<0.001$ vs Aβ.

FIGS. 9A-9B show that antisense oligonucleotides against N-SMase protect neurons from fibrillar Aβ toxicity in vivo in the cortex of C57/BL6 mice. One microgram of either ASO or ScO against N-SMase dissolved in 2 μl saline was stereotaxically injected into the frontal cortex. After 24 h of microinjection, 1 μg of fibrillar Aβ1-42 in 2 μl volume was again microinjected at the same site. After 24 h of the final microinjection, mice were perfused and double immunofluorescence (FIG. 9A) for NeuN (red) and TUNEL (green) was performed. Five mice (n=5) were used in each group. In FIG. 9B, TUNEL-positive cells as well as total DAPI-positive cells were counted in three cortical sections (two images per slide) of each of five different mice in an Olympus ΓX81 fluorescence microscope using the MicroSuite™ imaging software. Results are expressed as number of TUNEL-positive cells per 100 cells. $^a$p<0.001 vs saline; $^b$p<0.001 vs Aβ.

FIG. 10 shows that fibrillar Aβ alone is capable of activating N-SMase-ceramide pathway in neurons that leads to apoptosis and cell death (Jana and Pahan, 2004b, a). In astroglia, fibrillar Aβ-mediated activation of N-SMase-ceramide pathway is responsible for the activation of NF-κB and the expression of different proinflammatory soluble mediators including nitric oxide (NO). Once NO is produced, it can induce the expression of GFAP in astrocytes leading to astrogliosis. On the other hand, these glial-derived soluble mediators (e.g. NO) also induce neuronal apoptosis via N-SMase-ceramide pathway. It appears that multiple neurotoxic signaling pathways converge on N-SMase. 'SM' indicates sphingomyelin.

While only certain embodiments have been set forth, alternatives and modifications will be apparent from the above description to those skilled in the art. These and other alternatives are considered equivalents and within the spirit and scope of this disclosure and the appended claims.

The invention claimed is:

1. A method of treating a neurodegenerative disorder in a mammal in need thereof, the method comprising: administering a composition comprising GW4869 to the mammal to treat the neurodegenerative disorder.

2. The method of claim 1, comprising administering the composition to the mammal to treat the neurodegenerative disorder wherein the neurodegenerative disorder is selected from the group consisting of Alzheimer's disease, Parkinson's disease, multiple sclerosis, Huntington's disease and combinations thereof.

3. The method of claim 1, further comprising administering a composition comprising an antisense oligonucleotide against neutral sphingomyelinase.

4. The method of claim 3, wherein the antisense oligonucleotide is selected from SEQ. ID. NO. 12 and SEQ. ID. NO. 16.

* * * * *